(12) United States Patent
Sieben et al.

(10) Patent No.: US 10,254,216 B2
(45) Date of Patent: Apr. 9, 2019

(54) SYSTEMS, METHODS AND APPARATUS FOR ANALYSIS OF RESERVOIR FLUIDS USING SURFACE PLASMON RESONANCE

(71) Applicant: SCHLUMBERGER TECHNOLOGY CORPORATION, Sugar Land, TX (US)

(72) Inventors: Vincent Joseph Sieben, Cambridge, MA (US); Kenneth John Chau, Kelowna (CA); Shahnawaz Hossain Molla, Watertown, MA (US); Farshid Mostowfi, Lexington, MA (US); Elizabeth Jennings Smythe, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/638,443

(22) Filed: Jun. 30, 2017

(65) Prior Publication Data
US 2018/0003619 A1 Jan. 4, 2018

Related U.S. Application Data

(60) Provisional application No. 62/356,868, filed on Jun. 30, 2016.

(51) Int. Cl.
*G01N 21/05* (2006.01)
*G01N 21/25* (2006.01)
(Continued)

(52) U.S. Cl.
CPC .............. *G01N 21/27* (2013.01); *G01N 21/05* (2013.01); *G01N 21/553* (2013.01); *G01N 33/2835* (2013.01); *G01N 2021/258* (2013.01)

(58) Field of Classification Search
CPC .............. G01N 21/553; G01N 21/554; G01N 2021/5903; G01N 2021/258; G01N 21/648; G01N 21/658
See application file for complete search history.

(56) References Cited

U.S. PATENT DOCUMENTS 4,860,581 A 8/1989 Zimmerman et al.
5,804,453 A 9/1998 Chen
(Continued)

OTHER PUBLICATIONS

Abudu, A. et al., "Adsorption of Crude Oil on Surfaces Using Quartz Crystal Microbalance with Dissipation (QCM-D) under Flow Conditions," Energy and Fuels, 23(3), 2009, pp. 1237-1248.
(Continued)

*Primary Examiner* — Shawn Decenzo

(57) ABSTRACT

An optical sensor includes a flow cell permitting flow of a hydrocarbon-based analyte therethrough. A metallic film is disposed adjacent or within the flow cell. At least one optical element directs polychromatic light for supply to an interface of the metallic film under conditions of surface plasmon resonance (SPR) and directs polychromatic light reflected at the interface of the metallic film (which is sensitive to SPR at such interface and thus provides an SPR sensing region within the flow cell) for output to at least one spectrometer that measures spectral data of such polychromatic light. A computer processing system is configured to process the measured spectral data over time as the hydrocarbon-based analyte flows through the flow cell to determine SPR peak wavelength over time and to process the SPR peak wavelength over time to determine at least one property related to phase transition of the analyte.

38 Claims, 24 Drawing Sheets

(51) Int. Cl.
*G01N 21/27* (2006.01)
*G01N 33/28* (2006.01)
*G01N 21/552* (2014.01)

(56) References Cited

U.S. PATENT DOCUMENTS

| | | | |
|---|---|---|---|
| 6,058,773 | A | 5/2000 | Zimmerman et al. |
| 6,330,062 | B1 | 12/2001 | Corn et al. |
| 7,397,559 | B1 | 7/2008 | Bratkovski |
| 7,473,917 | B2 | 1/2009 | Singh |
| 8,169,617 | B2 * | 5/2012 | Ho ............... G01N 21/553 356/453 |
| 9,068,962 | B2 | 6/2015 | Schneider et al. |
| 9,249,661 | B2 | 2/2016 | Harrison et al. |
| 9,714,952 | B2 | 7/2017 | Feller et al. |
| 2003/0179379 | A1 | 9/2003 | Gedig |
| 2009/0021727 | A1 | 1/2009 | Sepulveda Martinez et al. |
| 2011/0171746 | A1 | 7/2011 | Fontaine et al. |
| 2011/0188043 | A1 | 8/2011 | Davidov et al. |
| 2011/0222066 | A1 | 9/2011 | Forcales et al. |
| 2014/0111809 | A1 * | 4/2014 | Kang ............... G01N 21/47 356/445 |
| 2014/0186215 | A1 * | 7/2014 | Shinta ............... G01N 21/554 422/69 |
| 2015/0233823 | A1 | 8/2015 | Echtermeyer |
| 2016/0097757 | A1 | 4/2016 | Sieben et al. |
| 2016/0116403 | A1 * | 4/2016 | Lear ............... G02B 6/1221 356/70 |

OTHER PUBLICATIONS

Adyani, W. N. et al., "A Systematic Approach to Evaluate Asphaltene Precipitation during C02 Injection", SPE 143903, presented at the SPE Enhanced Oil Recovery Conference, Kuala Lumpur, Malaysia, 2011, 27 pages.

Akbarzadeh, K. et al., "Introduction to a Novel Approach for Modeling Wax Deposition in Fluid Flows. 1. Taylor-Couette System", Industrial and Engineering Chemistry Research, 2008, 47(3), pp. 953-963.

Akbarzadeh, K. et al., "The Importance of Wax-Deposition Measurements in the Simulation and Design of Subsea Pipelines", SPE 115131, SPE Projects, Facilities and Construction, 2010, 5(2), pp. 49-57.

Bai, C. et al., "Thermal, Macroscopic, and Microscopic Characteristics of Wax Deposits in Field Pipelines", Energy & Fuels, 2013, 27(2), pp. 752-759.

Buckley, J.S., "Predicting the Onset of Asphaltene Precipitation from Refractive Index Measurements", Energy & Fuels, 1999, 13(2), pp. 328-332.

Buckley, J.S . et al., "Asphaltene Precipitation and Solvent Properties of Crude Oils", Petroleum Science and Technology, 1998, 16(3-4), pp. 251-285.

Gonzalez, D. L. et al., "Effects of Gas Additions to Deepwater Gulf of Mexico Reservoir Oil: Experimental Investigation of Asphaltene Precipitation and Deposition", SPE 159098, presented at the SPE Annual Technical Conference and Exhibition, San Antonio, Texas, USA, Society of Petroleum Engineers, 2012, 11 pages.

Hammami, A. et al., "Asphaltene Precipitation from Live Oils: An Experimental Investigation of Onset Conditions and Reversibility", Energy & Fuels, 1999, 14(1), p. 14-18.

Huang, Z. et al., "The Effect of Operating Temperatures on Wax Deposition", Energy & Fuels, 2011, 25(11), pp. 5180-5188.

Jamaluddin, A.K.M. et al., "A Comparison of Various Laboratory Techniques to Measure Thermodynamic Asphaltene Instability", SPE-72154, presented at the SPE Asia Pacific Improved Oil Recovery Conference, Kauala Lumpur, Malaysia, Society of Petroleum Engineers, 2001, pp. 17 pages.

Jamaluddin, A.K.M. et al., "An Investigation of Asphaltene Instability Under Nitrogen Injection", SPE 74393, presented at the SPE International Petroleum Conference and Exhibition, Villahermosa, Mexico, Society of Petroleum Engineers Inc., 2012, pp. 10 pages.

Jorgenson, R. C. et al., "A fiber-optic chemical sensor based on surface plasmon resonance", Sensors and Actuators: B. Chemical, 1993, 12(3), pp. 213-220.

Jorgenson, R. C. et al., "Control of the dynamic range and sensitivity of a surface plasmon resonance based fiber optic sensor", Sensors and Actuators: A. Physical, 1994, 43(1-3), pp. 44-48.

Joshi, N. B., et al., "Asphaltene Precipitation from Live Crude Oil", Energy & Fuels, 2001, 15(4), pp. 979-986.

Kalantari-Dahaghi, A. et al., "Formation Damage Through Asphaltene Precipitation Resulting From C02 Gas Injection in Iranian Carbonate Reservoirs" SPE Production & Operations, 2008, 23(2), pp. 210-214.

Mehfuz, R., "Improving the Excitation Efficiency of Surface Plasmon Polaritons Near Small Apertures in Metallic Films", 2013, The University of British Columbia: Okanagan, 140 pages.

Milhet M. et al., "Liquid-solid equilibria under high pressure of tetradecane + pentadecane and tetradecane + hexadecane binary systems", Fluid Phase Equilibria, 2005, 235(2), pp. 173-181.

Ooms, M. D. et al., "Surface Plasmon Resonance for Crude Oil Characterization", Energy & Fuels, 2015, 29(5), pp. 3019-3023.

Reimhult, E. et al., "Simultaneous Surface Plasmon Resonance and Quartz Crystal Microbalance with Dissipation Monitoring Measurements of Biomolecular Adsorption Events Involving Structural Transformations and Variations in Coupled Water", Analytical Chemistry, 2004, 76(24), pp. 7211-7220.

Sarica, C. et al., "Review of Paraffin Deposition Research under Multiphase Flow Conditions", Energy & Fuels, 2012, 26(7), pp. 3968-3978.

Schneider, M.H. et al., "Measurement of Asphaltenes Using Optical Spectroscopy on a Microfluidic Platform", Analytical Chemistry, 2013, 85(10), pp. 5153-5160.

Skinner, N. G. et al. "Downhole fiber optic sensing: the oilfield service provider's perspective: from the cradle to the grave", Proc. SPIE 9098, Fiber Optic Sensors and Applications, 2014, 18 pages.

Takagi, T. et al., "Refractive Index of Liquids under High Pressure", Journal of Chemical & Engineering Data, 1982, 27(1), pp. 16-18.

Tvakkoli, M. et al., "Asphaltene Deposition in Different Depositing Environments: Part 2. Real Oil," Energy & Fuels, 2014, 28(6), pp. 3594-3603.

Tvakkoli, M. et al., "Asphaltene Deposition in Different Depositing Environments: Part 1. Model Oil", Energy & Fuels, 2014, 28(3), pp. 1617-1628.

Wang, J. et al., "Asphaltene Deposition on Metallic Surfaces," Journal of Dispersion Science and Technology, 2004, 25(3), pp. 287-298.

"Standard Test Method for Determinatoin of Asphaltenes (Heptane Insolubles) in Crude Petroleum and Petroleum Products", ASTM D6560, 2005, 6 pages.

* cited by examiner

SYSTEMS, METHODS AND APPARATUS FOR ANALYSIS OF RESERVOIR FLUIDS USING SURFACE PLASMON RESONANCE

CROSS-REFERENCE TO RELATED APPLICATION(S)

The present disclosure claims priority from U.S. Provisional Patent Appl. No. 62/356,868, filed on Jun. 30, 2016, herein incorporated by reference in its entirety.

TECHNICAL FIELD

The present disclosure relates to methods and systems and apparatus that analyze reservoir fluids using surface plasmon resonance.

BACKGROUND

Asphaltenes are a sub-component of crude oil that form sticky aggregates when a shift in the native solubility matrix is caused by a change in pressure, temperature, or composition of the oil. The thermodynamics of asphaltene stability, the mechanisms of agglomeration, and the models for deposition are the focus of intense and active areas of research.

Unintended precipitation and deposition of asphaltene from reservoir fluids can happen during production, transportation, and processing operations. These deposits can lead to reservoir impairment, plugging near the wellbore, restriction in flowlines, as well as equipment failures and processing challenges for surface facilities. As such, flow assurance that accounts for possible precipitation and deposition of asphaltene from reservoir fluid relies heavily on frequent and accurate measurements, particularly when characterizing the asphaltene phase behavior within a crude sample.

Asphaltenes of a crude oil are conventionally defined as being poorly soluble in n-alkanes (e.g., n-heptane) and highly soluble in aromatic solvents (e.g., toluene). With this broad definition, the asphaltenes are a fraction of a crude oil sample that can vary from one crude oil sample to another. The complex mixture of asphaltene molecules can be characterized with a distribution of varying solubility parameters; ranging from the least soluble (less stable asphaltenes) to the most soluble (more stable asphaltenes). Gradual titration of stock tank crude oil or gradual depressurization of live crude oil is most often used to measure the solubility profile of the asphaltene fraction. The proportional amount of asphaltene precipitation can be measured by controllably sweeping the level of perturbation to the native crude oil. This profile can then be related to flow assurance control schemes and models. For example, as the amount of n-alkane (or titrant) is varied, only a fraction of the total amount of asphaltene precipitates. The remainder of asphaltenes stay in solution due to partial solubility. An asphaltene yield curve can be created by scanning a range of titrant-oil fractions, which is a plot relating the amount of precipitated asphaltenes as a function of titrant concentration. The data contained in the yield curve is related to asphaltene solubility or the phase separation of asphaltenes. Key parameters, like the asphaltenes precipitation onset point, can be extracted from such titration curves.

There are a number of techniques used to detect and measure the extent of asphaltene precipitation, including: visual observation, absorption and fluorescence spectroscopy, light scattering, refractive index-based methods, conductivity, acoustic resonance and filtration methods, viscosity, and the conventional gravimetric approach.

Currently, the asphaltene onset condition (pressure, temperature, and composition) in crude oil is determined by systematic depressurization (at constant temperature) of a sample of the crude oil in a PVT cell in the laboratory. In the PVT cell, precipitation of asphaltene is detected based on visual observation and light scattering. Another approach for detecting the onset of asphaltene precipitation and yield is to measure the crude oil refractive index during temperature, pressure, or composition perturbations. Buckley, J. S., *Predicting the Onset of Asphaltene Precipitation from Refractive Index Measurements*. Energy & Fuels, 1999, 13(2): p. 328-332 presents a graph of the measured refractive index (RI) for a mixture of n-heptane and oil. The mixture RI gradually decreases as n-heptane is added to a sample crude oil. When the asphaltene onset condition is reached, the mixture RI sharply decreases indicated by a difference in slopes. Sudden changes in RI indicate a phase transition. Surface plasmon resonance (SPR) spectra can also be used to determine the refractive index of the sample, which in turn may be used to measure solubility parameters of hydrocarbon fluids.

Furthermore, there are relatively few methods to monitor and characterize asphaltene deposition in real-time. Most often, a deposition experiment monitors the time-wise pressure change across a capillary tube or porous media while flowing crude oil through the system under specific conditions. The relative pressure change is determined using the Hagen-Poiseuille equation, assuming uniform deposition thickness on the wall surface along the entire flow-line length. When relating deposit thickness to pressure drop, it is further assumed that flow rate and viscosity remain constant. To achieve the required sensitivity, multiple pressure transducers with overlapping dynamic ranges are coupled to the entry port of a long stainless steel tube. It is necessary to have long tube lengths of 16-32 m with small cross-sections of 0.5 mm diameter and slow flowrates of approximately 5 mL/hr as described in Wang et al., "Asphaltene Deposition on Metallic Surfaces," Journal of Dispersion Science and Technology, Vol. 25(3), 2004, pgs. 287-298. Creating measurable deposits, 1-100 μm, often takes 50-100 hours or 2-4 days. Variations in deposition thickness, e.g. constricted regions or plugs, are not easily measured and detrimentally impact the apparent deposition thickness. Gradation can be accomplished with multiple sensor ports incorporated into the flow-line, but this creates added dead-volume and geometry changes at each pressure transducer junction. With flowline deposition experiments, one can also perform post-characterization of deposits in a batch-like manner. At the conclusion of the run, the surfaces of a Taylor-Couette device/chamber, or segments of the flowline, are rinsed with a solvent to capture the deposit, which is then concentrated and measured gravimetrically. These methods are excellent for detailed characterization of the deposit, but do not provide online feedback as the deposit is formed. Flowline deposition experiments therefore lack the sensitivity to observe initial adsorbed asphaltene layers and require significant runtimes.

Real-time observations of deposit formation have been made using a Quartz Crystal Microbalance with Dissipation (QCM-D) as described in Abudu et al., "Adsorption of Crude Oil on Surfaces Using Quartz Crystal Microbalance with Dissipation (QCM-D) under Flow Conditions," Energy and Fuels, Vol. 23(3), 2009, pgs. 1237-1248. The QCM-D measurements can be performed during titration experiments and achieve high mass sensitivity based on the electromechanical response of an oscillating piezoelectric sensor. Relating frequency shift and mass change in a vacuum or a gas environment can be accomplished with the Sauerbrey equation. QCM in a liquid environment like when immersed in crude oil is more complicated. The frequency shift depends on the chamber pressure, deposit mass loading (asphaltenes-viscoelastic films), liquid loading, liquid trapping, and surface roughness. Decoupling the deposited asphaltene mass from the other system attributes that impact the frequency shift requires tuned models. Often, correction factors and prior knowledge of the crude oil density and viscosity are required. Tavakkoli et al. performed a two-part detailed study of the factors influencing QCM-D measurements when coupled with titration experiments. See Tavakkoli et al., "Asphaltene Deposition in Different Depositing Environments: Part 1. Model Oil", Energy & Fuels, Vol. 28(3), 2014, pgs. 1617-1628; and Tavakkoli et al., "Asphaltene Deposition in Different Depositing Environments: Part 2. Real Oil," Energy & Fuels, Vol. 28(6), 2014, pgs. 3594-3603. They also evaluated deposition tendency using crystal surfaces coated with a variety of materials, including: gold, carbon steel, and iron oxide. Their work highlights the key advantages of QCM-D, namely: the sensitivity to detect nanograms of adsorbed mass, the ability to select relevant surface coatings, and fast measurement times (~hours). However, online QCM sensing of the deposit formation during flow conditions requires real-time thin-film density information to decouple entrapped fluid mass from asphaltene deposit mass. To solve a similar problem, Reimhult et al. combined QCM-D with surface plasmon resonance (SPR) to simultaneously measure the mass reported by both methods for an aqueous biomolecular system as described in Reimhult et al., "Simultaneous surface plasmon resonance and quartz crystal microbalance with dissipation monitoring measurements of biomolecular adsorption events involving structural transformations and variations in coupled water," Analytical Chemistry, Vol. 76(24), 2004, pgs. 7211-7220. QCM-D data was used to determine the total adsorbed thin-film mass (acoustically derived), while SPR data was used to determine the adsorbed biomolecule mass (optically derived) via refractive index of the thin-film decoupled from dynamically bound water. Reimhult et al. employed an iterative calculation process that incorporated physical models of the QCM-D/SPR approaches and determined accurate thin-film properties: thickness, density, total mass, water mass, and biomolecular mass. Lastly, realizing QCM-D devices at reservoir pressures that range from 5-30 kpsi will be challenging as most demonstrations with crude oil fluids are performed near atmospheric pressure. Studies show that it is feasible to build QCM systems rated to 3 kpsi, but thus far, the technique is generally limited to 5-6 kpsi.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In accordance with some examples, a novel optical sensor is provided that includes a flow cell that is configured to permit flow of a hydrocarbon-based analyte through the flow cell. A metallic film is disposed adjacent or within the flow cell. A light source is configured to generate polychromatic light. At least one optical element is configured to direct polychromatic light produced by the light source for supply to an interface of the metallic film under conditions of surface plasmon resonance and to direct polychromatic light reflected at the interface of the metallic film for output from the at least one optical element. The polychromatic light reflected at the interface of the metallic film is sensitive to surface plasmon resonance at the interface of the metallic film in order to provide an SPR sensing region within the flow cell. At least one spectrometer is operably coupled to the at least one optical element and is configured to measure spectral data of polychromatic light reflected at the interface of the metallic film as output by the least one optical element. A computer processing system is operably coupled to the at least one spectrometer and is configured to process the spectral data measured by the at least one spectrometer over time as the hydrocarbon-based analyte flows through the flow cell to determine SPR peak wavelength over time, and to process the SPR peak wavelength over time to determine at least one property related to phase transition of the hydrocarbon-based analyte.

In embodiments, the at least one optical element can include a prism (such as dove prism) disposed adjacent the metallic film can be part of a multilayer structure formed on one side of a substrate, wherein the multilayer structure interfaces to the flow cell and the opposite side of the substrate is disposed adjacent the prism. An index matching fluid can be disposed between the opposite side of the substrate and the prism.

In other embodiments, the least one optical element can include a fiber optic core with the metallic film bonded to the fiber optic core. The metallic film can be part of a multilayer structure bonded to the fiber optic core. The multilayer structure can surround a lengthwise segment of the fiber optic core, and the lengthwise segment of the fiber optic core can direct polychromatic light to the metallic film of the surrounding multilayer structure for reflection at the interface of the metallic film of the surrounding multilayer structure.

In embodiments, the least one optical element can further include a mirror formed at one end of the fiber optic core, wherein the mirror is configured to return polychromatic light reflected at the interface of the metallic film of the surrounding multilayer structure for output to a spectrometer. The mirror can be formed from the same metal as the metallic film of the multilayer structure.

In other embodiments, the fiber optic core can be configured to transmit polychromatic light reflected at the interface of the metallic film of the surrounding multilayer structure for output to a spectrometer.

In embodiment(s), the fiber optic core and metallic film (or the surrounding multilayer structure including the metallic film) can be part of a probe assembly that extends into the flow cell. The probe assembly can extend into the flow cell in a direction parallel to the flow through the flow cell, or in a direction transverse to the flow through the flow cell. A seal can provide a fluid seal between the probe assembly and the flow cell.

In embodiment(s), the metallic film can be part of a multilayer structure that interfaces to the flow cell or that extends into the flow cell. The multilayer structure can include a thin-film stack including a protective layer (e.g., Zirconium Dioxide) that covers the metallic film and/or a bonding layer (e.g., Titanium) formed under the metallic film. The metallic film can be gold or silver.

In embodiment(s), the optical sensor can include a polarizer coupled to the at least one optical element, wherein the polarizer is configured to split polychromatic light reflected at the interface of the metallic film into an s-polarized beam and a p-polarized beam. The at least one spectrometer can include a first spectrometer and a second spectrometer, wherein the first spectrometer is configured to measure spectral data of the s-polarized beam, and the second spectrometer is configured to measure spectral data of the p-polarized beam. The computer processing system can be operably coupled to the first and second spectrometers and can be configured to determine an absorbance spectrum for a given time interval by subtracting spectral data of the s-polarized beam from spectral data of the p-polarized beam. The computer processing system can be further configured to identify a peak in the absorbance spectrum over time in order to determine the SPR peak wavelength over time.

In other embodiment(s), the optical sensor can include a fiber splitter that directs polychromatic light produced by the light source for supply to the interface of the metallic film. The fiber splitter can be configured to direct polychromatic light produced by the light source to a first spectrometer and direct polychromatic light reflected at the interface of the metallic film for output to a second spectrometer. The computer processing system can be configured to determine an absorbance spectrum for a given time interval by subtracting spectral data determined by the measurements of the first spectrometer from spectral data determined by the measurements of the second spectrometer. The computer processing system can be further configured to identify a peak in the absorbance spectrum over time in order to determine the SPR peak wavelength over time.

In embodiment(s), the hydrocarbon-based analyte can be mixture of an asphaltene precipitant (e.g., n-heptane) and crude oil with varying volume fractions of the asphaltene precipitant over time, and the at least one property related to phase transition of the hydrocarbon-based analyte can characterize asphaltene deposition onset of the crude oil. The computer processing system can be further configured to employ a model that relates SPR peak wavelength to a refractive index of the crude oil. The model can be calibrated by experiments with mixtures of the asphaltene precipitant (e.g., n-heptane) and an asphaltene solvent (e.g., toluene) at different relative volume fractions such that SPR peak wavelengths produced by the model matches measured SPR peak wavelengths determined by the computer processing system. The computer processing system can be further configured to employ a correlation function that relates the refractive index of the crude oil to a density of the crude oil.

In embodiment(s), the property related to phase transition of the hydrocarbon-based analyte can be associated with at least one of:

i) detection of the formation of vapor or liquid phases of the hydrocarbon-based analyte induced by temperature and/or pressure changes;

ii) detection of liquid condensation from hydrocarbon vapors induced by temperature and/or pressure changes;

iii) detection of hydrate formation induced by temperature and/or pressure changes;

iv) detection of scaling or inorganic precipitation induced by composition, temperature and/or pressure changes;

v) detection of asphaltene onset induced by composition, temperature and/or pressure or changes; and vi) sample fluid typing by means of measuring the direction and/or magnitude of the SPR shift when undergoing phase change.

In embodiment(s) the optical sensor can include a pressure control system for controlling pressure of the hydrocarbon-based analyte flowing through the flow cell over time. The pressure control system can be configured to vary pressure conditions of the hydrocarbon-based analyte flowing through the flow cell over one or more time intervals, or configured to maintain constant pressure conditions of the hydrocarbon-based analyte flowing through the flow cell over one or more time intervals. The optical sensor can further include a temperature control system for controlling temperature of the hydrocarbon-based analyte flowing through the flow cell over time. The temperature control system can be configured to vary temperature conditions of the hydrocarbon-based analyte flowing through the flow cell over one or more time intervals, or maintain constant temperature pressure conditions of the hydrocarbon-based analyte flowing through the flow cell over one or more time intervals.

In embodiment(s), the optical sensor can be part of a downhole tool.

In other embodiment(s), the optical sensor can be part of surface-located equipment at a well-site, fluid collection system, fluid processing system, or pipeline.

In still other embodiment, the optical sensor can be part of a laboratory apparatus.

BRIEF DESCRIPTION OF THE DRAWINGS

Those skilled in the art should more fully appreciate advantages of various embodiments of the present disclosure from the following "Description of Illustrative Embodiments," discussed with reference to the drawings summarized immediately below.

DETAILED DESCRIPTION

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The term "surface plasmon resonance" or "SPR" as used herein describes a condition in which light incident onto a surface of a highly conductive metallic film couples into resonant charge oscillations of the metallic film, resulting in light that is effectively trapped to the surface of the metallic film. In this trapped state, the light is sensitive to the dielectric environment in the immediate vicinity of the opposite surface of the metallic film (i.e., less than 1 μm away from the opposite surface of the metallic film). This condition is useful for detection of properties of an analyte that is deposited or located in the immediate vicinity of the opposite surface of the metallic film.

A Surface Plasmon Resonance (SPR) sensor analyzes a fluid under a condition in which light couples to charge oscillations at the surface of a metal, where the probing field penetrates in the immediate vicinity of the opposite surface of the metallic film (i.e., less than 1 μm away from the opposite surface of the metallic film). When mass adheres to the surface of the metal, the native thin-film resonant frequency shifts. SPR sensors are based on the Kretschmann configuration in which polarized light is directed by a high-index prism onto a thin metal film. A reduction in the light intensity reflected from the metal film can be interrogated by varying the angle of incidence of the light beam onto the thin metal film.

Figure 1:
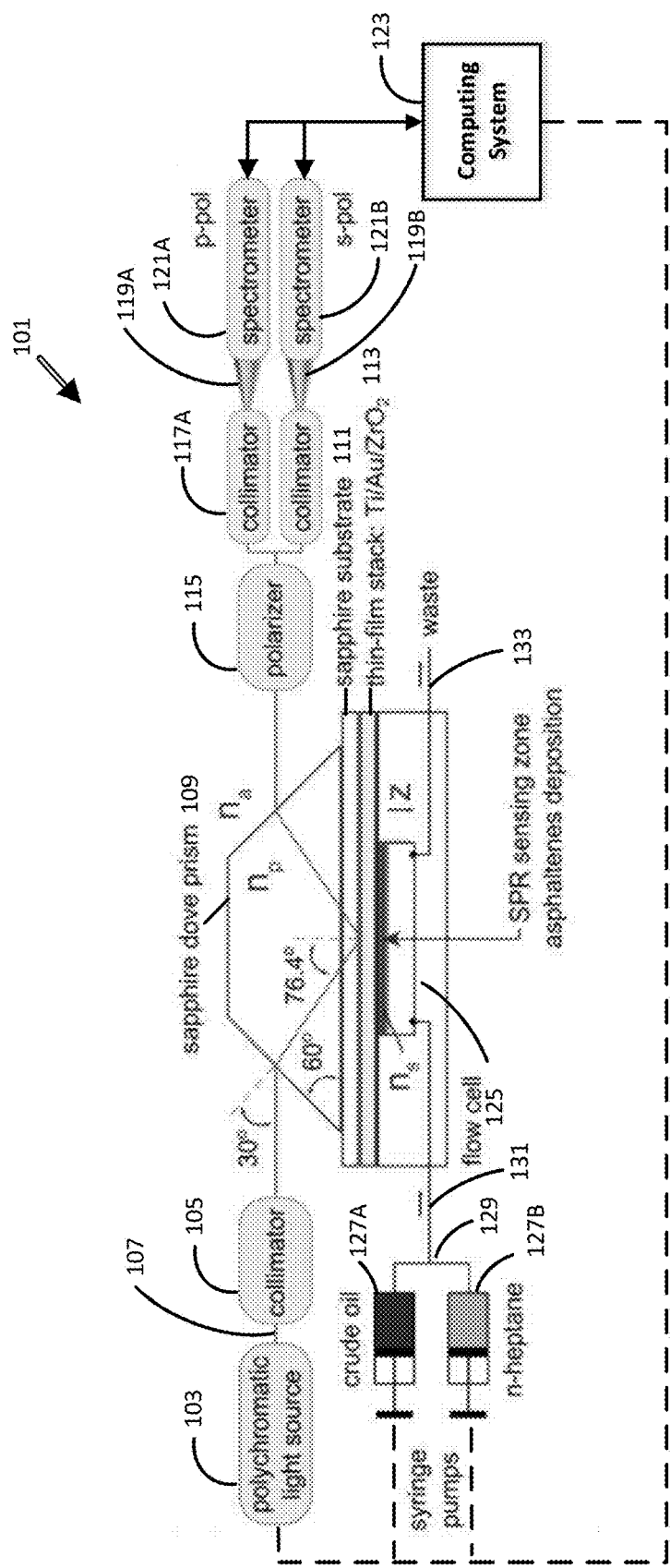
FIG. 1 is a schematic illustration of surface plasmon resonance (SPR) sensor according to the present disclosure.

In accordance with the present disclosure, an SPR sensor 101 as shown in FIG. 1 is provided that avoids the utilization of moving parts as is typically required by SPR sensors that vary the angle of incidence of the light beam onto the thin metal film. The SPR sensor 101 can possibly sacrifice resolution with readily available spectrometers, but can provide faster acquisition times and is more amenable to ruggedized applications, such as part of a downhole tool that experiences high pressure high temperature conditions of a downhole wellbore environment or as part of a surface-located system at a wellsite or pipeline. The SPR sensor 101 includes a polychromatic light source 103 (for example, the HL-2000 tungsten halogen white light source 360-2400 nm commercially available from Ocean Optics, USA) that is coupled to a collimator 105 (for example, the F240SMA-B collimator commercially available from Thorlabs, USA) using a light guide 107 (such as a 2 m long 0.22 NA-200 μm core SMA-SMA M92L02 fiber patch cable commercially available from Thorlabs, USA). The collimated beam produced by the collimator 105 is then passed through an adjustable iris (not shown) to produce a light beam 107 that is coupled to a prism 109. In one embodiment, the prism 109 is a dove prism realized from sapphire material. The prism can have a long side of 70.81 mm, a width and height of 15 mm, a short side of 53.49 mm, and angled faces at 600 to the long side, with a crystallographic orientation where the c-plane is aligned to the 70.81×15 mm and 53.49×15 mm faces. The prism 109 directs the incident light beam to a substrate 111 with a thin-film stack 113 formed on the bottom-side of the substrate 111 as shown. An index matching fluid (for example, refractive index-matching liquid 18152 commercially available from Cargille, USA with a refractive index of 1.77) can be disposed between the prism 109 and the substrate 111. In one embodiment, the substrate 111 is formed of sapphire material and is 1 mm thick. The thin-film stack 113 includes a series of layers formed on the substrate 111. In one embodiment, the series of layers of the thin-film stack 113 includes a layer of Titanium (Ti) of approximately 5 nm in thickness (adhesion layer), which is formed below a layer of Gold (Au) of approximately 50 nm in thickness (primary plasmonic layer), which is formed below a layer of Zirconium dioxide ($ZrO_2$) of approximately 15 nm in thickness (protection layer). In other embodiments, Silver (Ag) can also be used as the plasmonic layer to attain sharper SPR spectra with higher sensitivity, and other protective coatings such as Titanium dioxide ($TiO_2$) can be used depending on requirements. Note that adding a protection layer realized from a dielectric material like $ZrO_2$ may result in guided-wave SPR or coupled-wave SPR, particularly if the protection layer is thick enough (i.e., approximately a few hundreds of nanometers in the visible) to support guided modes. In the embodiment above, the protective layer is much thinner (i.e., approximately a few tens of nanometers) than the cutoff thickness required to support the higher order guided modes. However, with thin layers of high refractive index material there is partial wave guiding that can occur. In these situations, the wave guide material can be thin enough such that a large fraction of the evanescent wave will be exposed to the analyte, thereby enhancing SPR sensitivity. The light beam reflected at the interface of the substrate 111 and the thin-film stack 113, which has intensity loss due to SPR at each wavelength, passes through the prism 109 and is directed to a polarizer 115 (for example, the CM1-PBS252 polarizer commercially available from Thorlabs, USA). The polarizer 115 separates this reflected light beam into a p-polarized beam and an s-polarized beam, which are each collimated by respective collimators 117A, 117B into separate light guides 119A, 119B (e.g., fiber patch cables) for supply to corresponding spectrometers 121A, 121B (for example, UV-VIS spectrometers, HR2000+CG-UV-NIR, with a usable wavelength range 200-1100 nm commercially available from Ocean Optics, USA). The spectrometer 121A measures the spectra of the p-polarized beam (which represents the intensity of the p-polarized beam over a number of different wavelengths), while the spectrometer 121B measures the spectra of the s-polarized beam (which represents the intensity of the s-polarized beam over a number of different wavelengths).

A programmed computing system 123 (such as a PC or workstation) acquires the spectra of the p-polarized beam from the spectrometer 121A and the spectra of the s-polarized beam from the spectrometer 121B. It also performs data storage and analysis of the p-polarized beam spectra and the s-polarized beam spectra to determine an SPR peak wavelength. In embodiment(s), the SPR peak wavelength can be extracted from the p-polarized beam spectra and the s-polarized beam spectra in two steps. First, an absorbance spectrum can be calculated by dividing a characteristic spectrum of the p-polarized beam (which can be determined by averaging the p-polarized beam spectra per wavelength as measured by the spectrometer 121A over a given measurement time interval) by a characteristic spectrum of the s-polarized beam (which can be determined by averaging the s-polarized beam spectra per wavelength as measured by the spectrometer 121B over the same measurement time interval). Note that s-polarized light does not couple to surface plasmons. Therefore, the s-polarized beam that is measured by the spectrometer 121B does not experience SPR losses and provides a reference spectrum. Second, a peak detection algorithm is used to determine the SPR peak wavelength from the absorbance spectrum. The SPR peak wavelength can be plotted versus time to observe the evolution of the SPR peak wavelengths during one or titration experiments as described herein. Furthermore, a calibrated model can be used to convert the SPR peak wavelength(s) into an effective refractive index for interpretation. An exemplary calibrated model is described herein.

The SPR sensor 101 includes a flow cell 125 with a chamber disposed adjacent the thin-film stack 113 (e.g., adjacent the protection layer of the thin-film stack 113). In embodiments, the flow cell 125 can be formed from an aluminum block with a well-defined total internal dead-volume (for example, 42.5 μL). Fluid flows through the chamber of the flow cell 125, which includes an SPR sensing zone in the vicinity where the light beam is reflected at the interface of the substrate 111 and the thin-film stack 113 as shown in FIG. 1. Note that the SPR sensing zone is located on top of the fluid flow through the chamber of the flow cell 125 to ensure gravitational settling was not the primary mechanism for detecting asphaltene deposition as described herein.

A sample of crude oil (e.g., reservoir fluid) is loaded into a syringe pump 127A. N-heptane (e.g., the titrant and a precipitant of asphaltenes) is loaded into a syringe pump 127B. The crude oil output of the syringe pump 127A and the n-heptane output of the syringe pump 127B is supplied a Y-connector 129 to form a mixture of the two fluid components, which is directed to the flow cell 125 by tubing 131. A check valve (not shown) can be fluidly coupled between the syringe pump 127B and the Y-connector 131 to prevent backflow, if desired. Waste from the flow cell 125 is directed by tubing 133 to a waste container (not shown). The computing system 123 can interface to the syringe pumps 127A, 127B to provide automatic control over the flow rate of the crude oil output of the syringe pump 127A as supplied to the Y-connector 129 and the flow rate of the n-heptane output of the syringe pump 127B as supplied the Y-connector 129. In this manner, the computing system 123 can provide automatic control the relative concentrations of the crude oil and the n-heptane in the mixture supplied to the flow cell 125 for the titration experiments as described herein.

In embodiment(s), the SPR sensor 101 is designed for a range of refractive indices that spans 1.4-1.7, as is expected for crude oil. The dynamic range of measurable refractive indices can be tailored by changing the metallic and protective layer materials and thicknesses of the thin-film stack 113.

The SPR sensor 101 as described above can be configured to carry out one or more titration experiments. The SPR sensing zone of the flow cell 125 can be filled with toluene between titration experiments. The titration experiment begins by the computer system 123 controlling the syringe pumps 127A, 127B to inject a mixture of the crude oil and n-heptane into the flow cell 125, which displaces the toluene stored in the tubing and flow cell 125. This can be accomplished by a ramp infusion of both the crude oil and n-heptane. In embodiments, the crude oil can be initially injected at 480 L/min and the n-heptane at 20 L/min. The combined flow rate was maintained at 500 μL/min yielding a residence time of 21.5 seconds from Y-connector 129 to the flow cell output. Over the course of one hour, the crude oil flow rate can be linearly ramped down to 240 μL/min and the n-heptane flow rate can be linearly ramped up to 260 μL/min. This provided a continuous n-heptane:oil volume ratio that spans from 0.04 to 1.08. At regular intervals (e.g., every one second) during the titration experiment as the n-heptane:oil volume ratio is continuously varied over this range, the computing system 123 determines the SPR peak wavelength from the spectra of the p-polarized beam and the spectra of the s-polarized beam as measured by the spectrometers 121A, 121B as described above. After the titration experiment, the system can be flushed with toluene and stored until the next experiment.

In embodiment(s), the mixing of the crude oil and n-heptane streams can be accomplished in the laminar flow regime, meaning that the mixing is governed largely by diffusion across the cross-sectional area of the tubing 131. After the Y connector 129 (i.e., mixing junction), there are two side-by-side streams, one of n-heptane and one of crude oil. Since n-heptane is the smaller and faster diffusing molecule, it will set the characteristic time for mixing. The length of the tubing 131 can be configured to allow for the desired diffusion of the n-heptane within the cross-sectional diameter of the tubing 131. Also, the kinetics near the onset of asphaltene deposition are particularly slow, often requiring hours or days to form micron sized asphaltene aggregates. The ability of SPR sensor 101 to detect nanometer-sized asphaltene depositions circumvents the need to wait for asphaltene aggregates to reach a microscopically detectable size (~1 μm).

Figure 2A:
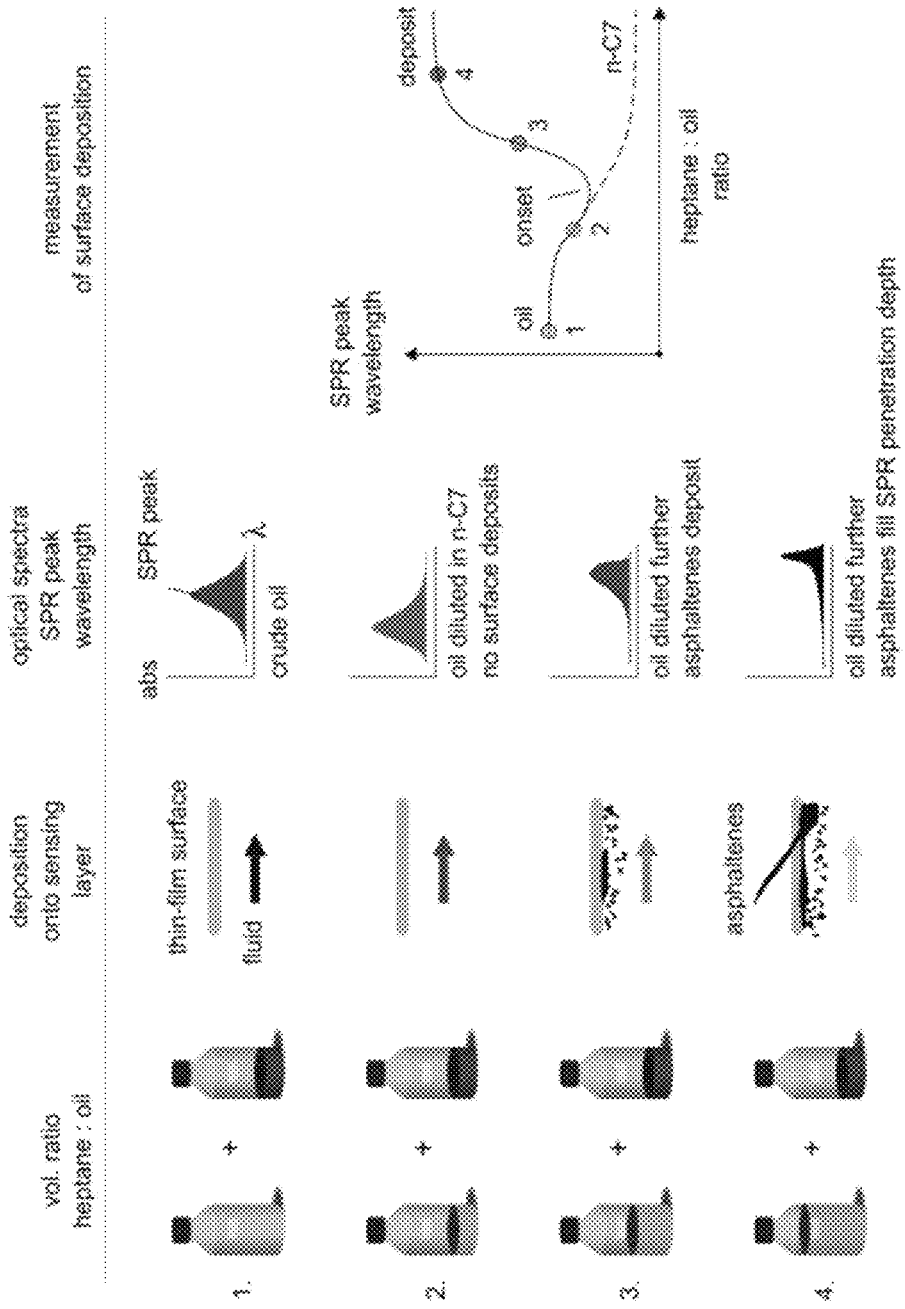
FIG. 2A is a schematic illustration of a titration experiment carried out with the SPR sensor of FIG. 1 in order to measure asphaltene deposition onset of a crude oil or other hydrocarbon bearing fluid.

The methodology of the titration experiment is shown in FIG. 2A. In embodiment(s), all measurements can be performed at room temperature between 21-24° C. and 1 atmosphere of pressure. Initially, the crude oil alone (without any n-heptane) is flowed through the flow cell 125, and the computing system 123 determines the SPR peak wavelength that is characteristic of the crude oil, which is labeled as point "1" in the graph on the right side of FIG. 2A. The SPR peak wavelength depends on the refractive index of the crude oil, where high density oils typically have higher refractive indices and thus longer SPR peak wavelengths. As n-heptane is added, the computing system 123 determines the SPR peak wavelength, which will blue-shift toward shorter wavelengths—labeled as point "2" in the graph on the right side of FIG. 2A. This is because the SPR sensor 101 is detecting the diluted crude oil, which has a lower refractive index-tending toward n-heptane. However, at a certain point, the amount of added n-heptane will induce asphaltene precipitation that may lead to deposition. Although the diluted crude oil fluid has a lower refractive index at higher titration ratios, the asphaltenes are denser and have a higher refractive index. If a deposit of asphaltenes forms in the SPR sensing zone, the computing system 123 will determine an SPR peak wavelength that starts to red-shift to longer wavelengths—labeled as point "3" in the graph on the right side of FIG. 2A. The amount of n-heptane is further increased in relation to the crude oil, leading to the precipitation and deposition of the otherwise more soluble asphaltenes. This continues until the deposit formed is thick enough to completely fill the SPR sensing zone and a plateau is reached—labeled as point "4" in the graph on the right side of FIG. 2A. Here the SPR sensor 101 becomes blind to any further deposition of asphaltenes, but the final plateau wavelength provides an indication on the density of the asphaltene deposit within the SPR sensing zone.

Figure 2B:
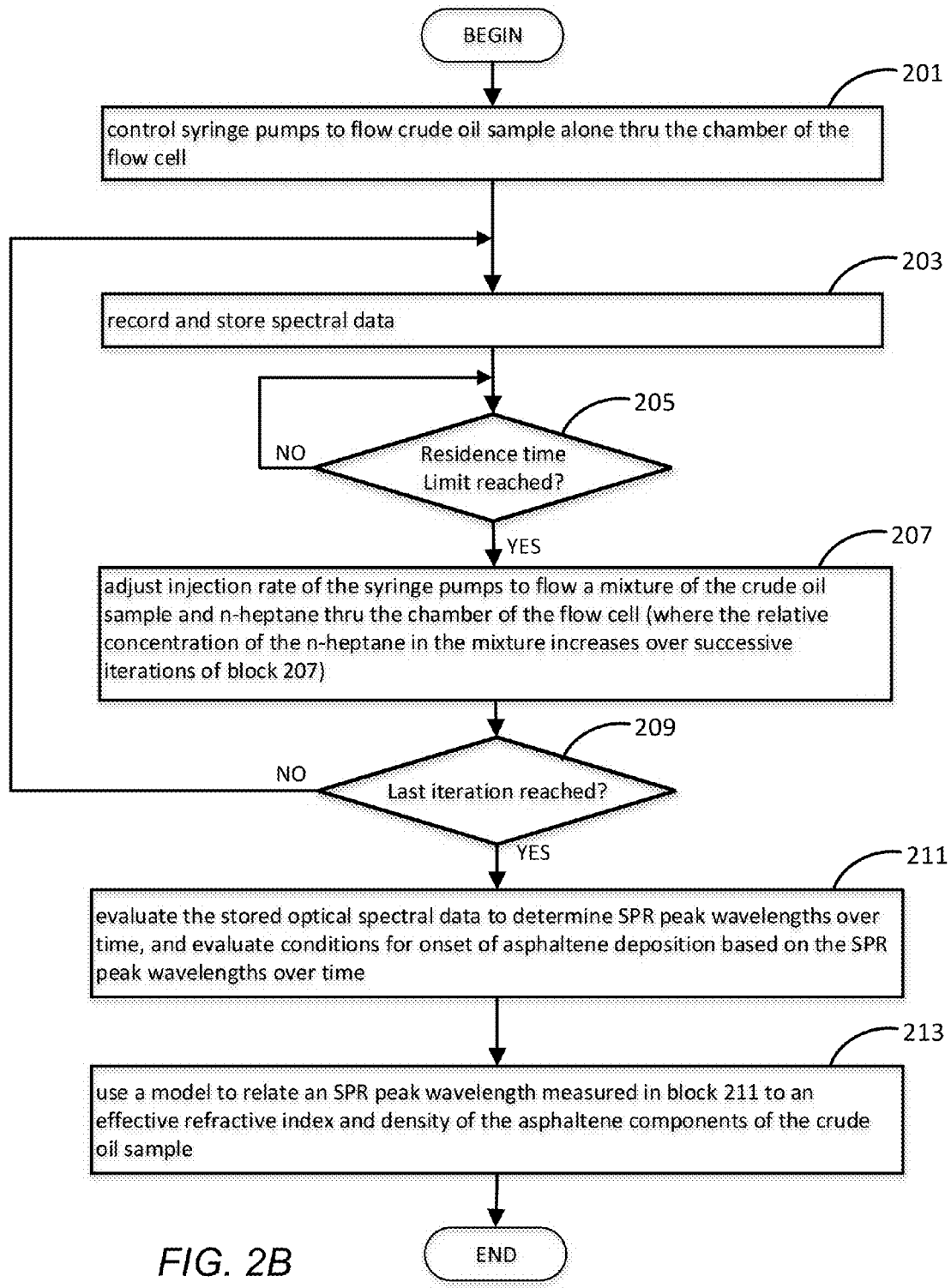
FIG. 2B is a flowchart of a workflow of the titration experiment of FIG. 2A.

Exemplary operations of the titration experiment of FIG. 2A is shown in FIG. 2B, which begins in block 201 where the computer processing system 123 controls the syringe pumps 127A, 127B to flow the crude oil sample alone thru the chamber of the flow cell 125.

In block 203, the computer processing system 123 records and stores the p-polarized spectral data output by the spectrometer 121A as well as the s-polarized spectral data output by the spectrometer 121B as the crude oil sample alone flows thru the chamber of the flow cell 125.

In block 205, the computer processing system 123 waits for expiration of a residence time limit and then proceeds to block 207.

In block 207, the computer processing system 123 is configured to adjust the injection rate of the syringe pumps 127A, 127B to flow a mixture of crude oil sample and n-heptane thru the chamber of the flow cell (where the relative concentration of the n-heptane in the mixture increases over successive iterations of block 207).

In block 209, the computer processing system 123 determines if the last iteration of the injection rate adjustment has been performed. If not, the operations returns to block 203 to record and store the p-polarized spectral data output by the spectrometer 121A as well as the s-polarized spectral data output by the spectrometer 121B as the mixture of the crude oil sample and n-heptane flows thru the chamber of the flow cell 125, and block 205 to wait for expiration of a residence time limit and then proceed to block 207 for adjusting the relative concentration of the n-heptane in the mixture for the next iteration. If yes, the operations continue to block 211.

In block 211, the computer processing system 123 can be configured to evaluate the stored optical spectral data to determine SPR peak wavelengths over time, and evaluate conditions for onset of asphaltene deposition based on the SPR peak wavelengths over time.

In block 213, the computer processing system 123 can be configured to use a model to relate the SPR peak wavelength measured by the SPR sensor in block 211 to an effective refractive index as well as density of the asphaltene components of the crude oil sample.

In other embodiment(s), the titration experiments as described herein can substitute the n-heptane with another precipitant of asphaltenes, such as n-hexane, n-pentane, petroleum ether, ethyl acetate, alcohols and any other fluid that precipitates asphaltenes.

In embodiment(s), a model of the SPR sensor 101 can be used to relate the SPR peak wavelength measured by the SPR sensor 101 to a refractive index of the crude oil. In one embodiment, the model employs a matrix formalization that account for the multi-layered system, including the prism, index matching fluid, substrate, thin-film stack layers (Ti/Au/ZrO2), and sensed fluid/deposit layer. For the SPR sensor 101, the s-polarized and p-polarized reflected light intensity at each wavelength can be calculated as:

$$R^{s,p} = \frac{I_{out}^{s,p}}{I_{in}^{s,p}} = |r^{s,p}|^2 \tag{1}$$

$$\text{where } r^{s,p} = \frac{M_{21}^{s,p}}{M_{11}^{s,p}}, \text{ and} \tag{2}$$

$$\begin{pmatrix} E_i \\ E_r \end{pmatrix} = M^{s,p} \begin{pmatrix} E_t \\ 0 \end{pmatrix}, \tag{3}$$

where R is the reflectance, $I_{in}$ and $I_{out}$ are the input incident light intensity and the output reflected light intensity of the beam propagating inside the prism 109, respectively;

r is the reflection coefficient, and M is the matrix representation of the substrate 111 and thin-film stack 113 that links the incident, reflected and transmitted electric field amplitudes ($E_i, E_r, E_t$). The superscripts s or p signify either s- or p-polarized light.

The matrix representation of the multi-layered system can be calculated as:

$$M^{s,p} = \begin{pmatrix} M_{11} & M_{12} \\ M_{21} & M_{22} \end{pmatrix} = D_0^{-1} \left[ \prod_{l=1}^{N} D_l P_l D_l^{-1} \right] D_s \tag{4}$$

$$D_l = \begin{cases} \begin{pmatrix} 1 & 1 \\ n_l \cos\theta_l & n_l \cos\theta_l \end{pmatrix}, & \text{for } s \text{ pol} \\ \begin{pmatrix} \cos\theta_l & \cos\theta_l \\ n_l & n_l \end{pmatrix}, & \text{for } p \text{ pol} \end{cases} \tag{3}$$

$$P_l = \begin{pmatrix} e^{ik_l d_l} & 0 \\ 0 & e^{-ik_l d_l} \end{pmatrix}, \text{ where } k_l = n_l \frac{w}{c} \cos\theta_l \tag{6}$$

where N is the number of layers (l=0, 1, 2, ..., s) in the multi-layered system, $D_l$ is the dynamical matrix for the respective layer l of the multi-layered system, and $P_l$ is the associated propagation matrix for the respective layer l of the multi-layered system. For each respective layer l of the multi-layered system, $n_l$ is the complex index of refraction, $\theta_l$ is the complex angle of propagation, $k_l$ is the component of the wave vector along the direction of propagation, $d_l$ is the thickness of the layer, and w is the angular frequency of light. The incident medium is l=0 and the sample medium is l=s; where, the layer stack order is substrate (sapphire)-adhesion layer (titanium)-plasmonic layer (gold)-protection layer (zirconium dioxide)-hydrocarbon.

For the multi-layered stack, the layer thicknesses are known for sapphire, titanium, gold, and zirconium dioxide. Also, the refractive indices for the sapphire, titanium, gold, and zirconium dioxide layers are readily available from the literature or they can be measured for each sensor for improved accuracy. The wavelengths, angular frequencies, and the complex angles of propagation are known. The reflected light intensities by wavelength are also known, as measured by the spectrometer. Thus, from the model, the remaining unknowns are the "effective complex refractive index" of the sample at each wavelength and the depth or thickness of the sensed layer. It is assumed that the sample is homogenous and that it completely fills the SPR penetration depth with a sufficiently large thickness. Therefore, the effective refractive index of the sample can be determined by numerical iteration.

The use of a complex angle of propagation is required to accommodate the evanescent waves. Complex refractive indices as functions of wavelength from the literature were also used for the various materials. As the index of refraction used in these equations is represented by a complex number, it mathematically incorporates both a) the attenuation losses via the imaginary part and b) the phase velocity changes via the real part. Therefore, equations 1-6 are generalized and account for both attenuation and phase velocity changes. In the case of heptane-toluene solutions used for calibration, the assumption is that the absorption from 500-800 nm is negligible and thus the imaginary part is insignificant and the Lorentz-Lorenz equation is used to determine the effective refractive indices for various mixtures. However, in the case of crude oil, there may be a minor degree of attenuation at these wavelengths and this will be addressed in future sections. Software code (such as Matlab code) can be written to implement the above model and perform the calculations over a range of wavelengths (400 nm-900 nm) and incident angles (76-77°).

The model of the SPR sensor 101 can be calibrated or tuned using mixtures of n-heptane (a precipitant of asphaltenes) and toluene (a solvent that dissolves asphaltenes). The syringe pump 127A is loaded with toluene and the syringe pump 127B is loaded with n-heptane. Initially, the syringe pumps 127A, 127B can be configured to flow toluene alone through the flow cell 125 at a desired flow rate (for example, at 1 mL/min for 5 minutes). Next, the syringe pumps 127A, 127B are configured to flow toluene and n-heptane through the flow cell 125 at flow rates (e.g., toluene at 0.0.9 mL/min and n-heptane at 0.1 mL/min for 4 minutes) yielding an n-heptane:toluene volume fraction of 0.1. The volume fraction was then successively incremented by steps of 0.1 (preferably for 4 minutes at each step). Finally, the syringe pumps 127A, 127B can be configured to flow n-heptane alone through the flow cell 125 at a desired flow rate (for example, at 1 mL/min for 5 minutes), followed by a flush with toluene. The spectra of s-polarized light and the p-polarized light can be collected by the spectrometers 121A, 121B continuously during this process. The s-polarized light undergoes total internal reflection and does not lose intensity due to excitation of surface plasmons, providing simultaneous correction of baseline shifts in light intensity. The computer system 123 can determine the SPR peak wavelength of the absorbance spectrum versus the variable n-heptane:toluene volume fractions of the calibration process. The computer system 123 can also be configured to use the model of the SPR sensor 121 as described above to determine the SPR peak wavelength for different n-heptane:toluene volume fractions used in the calibration process. The computer system 123 can adjust or tune certain parameters of the model (such as the refractive index of the zirconium dioxide layer of the thin-film stack) such that the SPR peak wavelengths produced by the model matches the measured SPR peak wavelengths determined by the computer system 123 at different n-heptane:toluene volume fractions used in the calibration process. Note that the calibrated or tuned model can be used to determine the effective refractive index of the crude oil from the SPR peak wavelength measured by the SPR sensor 101. In other embodiments, the model of the SPR sensor 101 can be calibrated or tuned using mixtures where the n-heptane is substituted by some other precipitant of asphaltenes (such as n-hexane, n-pentane, petroleum ether, ethyl acetate, alcohols and any other fluid that precipitates asphaltenes), and the toluene is substituted by some other solvent that dissolves asphaltenes (such as dichloromethane (DCM), xylenes, benzene, methyl naphthalene, cyclohexane, tetrahydrofuran (THF), chloroform, trichloroethylene, tetrachloroethylene, carbon tetrachloride, and any other fluid that dissolves asphaltenes).

The effective refractive index of the crude oil can be related to density of the crude oil based on a correlation determined from the results of crude oils with known densities. In one example, correlation has been used to relate the refractive index (RI) of the crude oil can to density ($\rho$) of the crude oil (in grams/cm$^3$) as follows:

$$\rho = (3.0983RI)3.7978. \qquad (7)$$

Figure 3A:
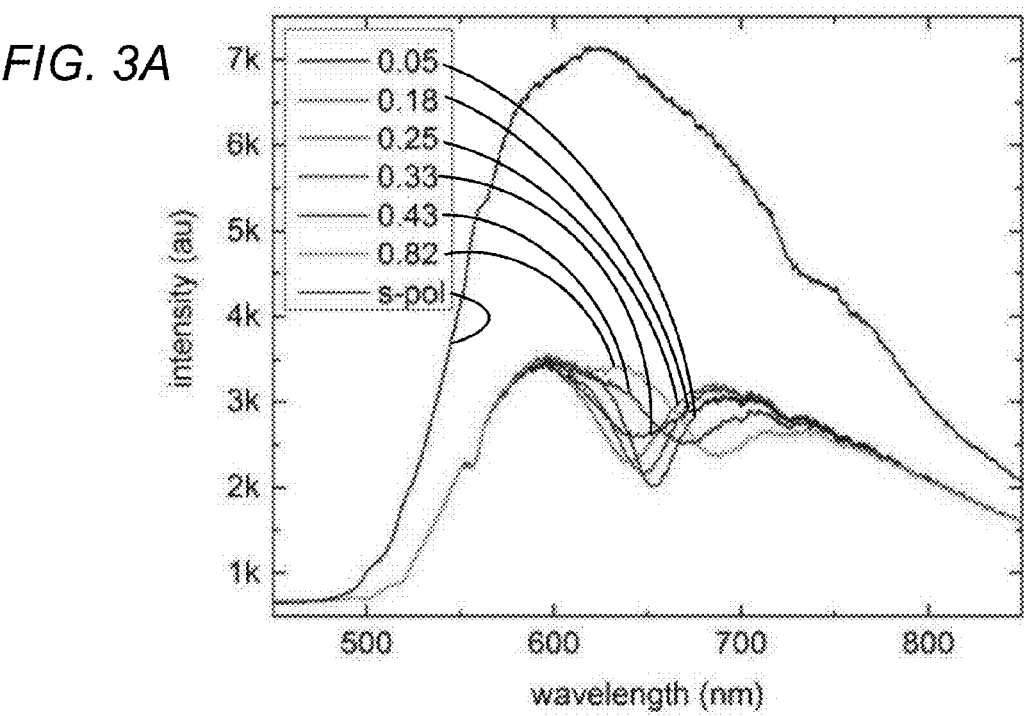
FIG. 3A are plots of the spectra measured by the spectrometers of the SPR sensor of FIG. 1 as part of an exemplary stepwise titration experiment following the workflow of FIG. 2B.
Figure 3B:
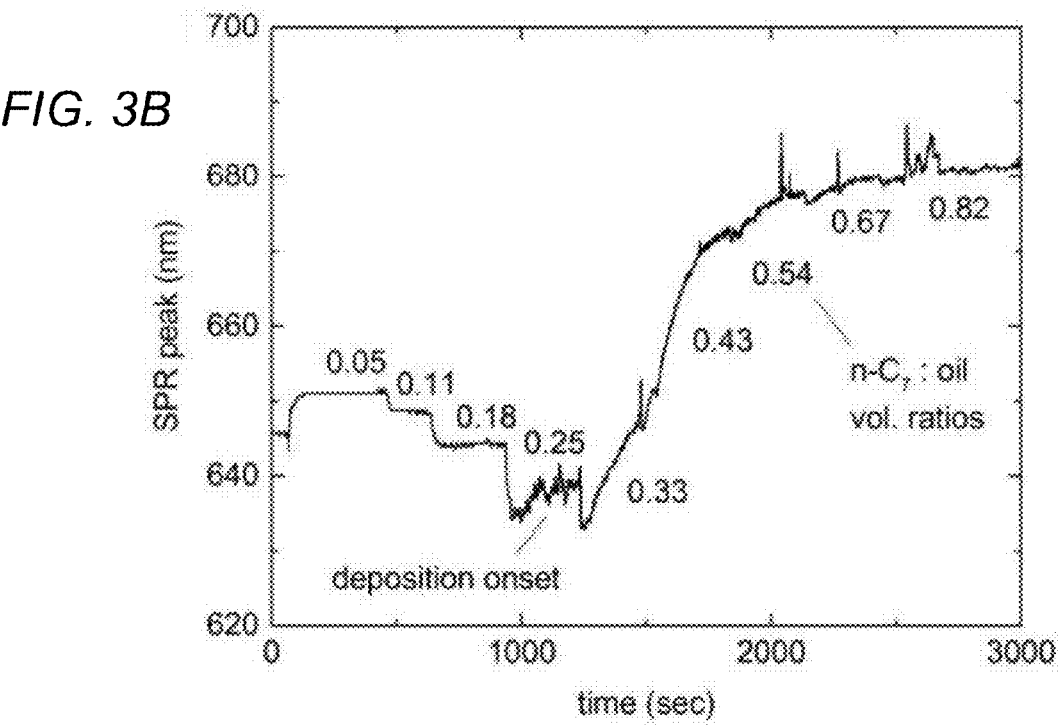
FIG. 3B is a plot of SPR weak wavelength over time, which is determined by the SPR sensor of FIG. 1 as part of the exemplary stepwise titration experiment of FIG. 3A.

To assess the suitability of the SPR sensor 101 in measuring asphaltene deposition onset, a stepwise titration experiment of a representative crude oil was performed while the optical spectra and SPR peak wavelength were recorded. The representative crude oil had a density of 0.8844 g/cm$^3$ and an API of 28.5. The representative crude oil had the following compositional components by weight percentage, 54.4% saturates, 21.9% aromatics, 18.8% resins, and 4.3% asphaltenes. FIGS. 3A and 3B shows the SPR data acquired from the stepwise titration experiment of the representative crude oil with n-heptane. FIG. 3A shows the light intensity spectra for a selected number of n-heptane:oil volume ratios, and FIG. 3B shows the SPR peak wavelength versus time as the n-heptane:oil volume ratio was varied over time. The SPR peak wavelength is well defined at 651 nm for a volume ratio of 0.05, approximately that of the neat crude oil-650 nm. As more n-heptane is added, the SPR peak wavelength shifts downward to 648 nm at a volume ratio of 0.11 and further to 644 nm at a volume ratio of 0.18. The dilution of crude oil with n-heptane produces blue-shifting SPR peaks (FIG. 3A) and the expected decline in SPR peak wavelength (FIG. 3B). When the volume ratio is 0.25, asphaltene deposition has occurred and localized surface depositions are initiated-likely the source of the noisy SPR peak wavelength signal. As the volume ratio increases to 0.33, the deposition rate increases and is marked by the abrupt rise in the SPR peak wavelength. At higher volume ratio of 0.43, the deposition rate increases with a steeper slope and continues until reaching the maximum penetration depth of the SPR sensing zone. The final SPR peak wavelength (i.e., refractive index) of the surface deposit is higher than that of the initial crude oil, indicating the heavy crude oil components (i.e., asphaltenes) are concentrated and adsorbed on the sensor surface. Diluted crude oil may also be trapped within the asphaltene deposit layer. The formation of the deposit layer can be observed by the broadening and red-shifting SPR peak wavelengths (FIG. 4A) and the rising SPR peak wavelength (FIG. 4B). The sensing surface was purposefully placed on top of the fluid flow, and the results indicate that the primary mechanism of deposition was not gravitation settling of the asphaltene particles.

For the representative crude oil, the asphaletene deposit has an SPR peak wavelength of approximately 680 nm corresponding to an effective refractive index of 1.539, or 0.028 refractive index units higher than the native crude oil. Using the density correlation of Eqn. 7, the estimated density of the deposit is 0.970 g/cm$^3$, compared to the initial crude oil density of 0.884 g/cm$^3$, indicating that deposit consists of the heavier components within the crude oil.

To further assess the performance of the SPR sensor 101 in measuring asphaltene deposition onset, ramped titration experiments of three representative crude oils was performed while the optical spectra and SPR peak wavelength were recorded. A ramped titration provides a more continuous sweep of n-heptane:crude oil volume ratio, allowing finer resolution in measuring the onset of asphaltene deposition. The three representative crude oils are referred to as crude oil 1, crude oil 2 and crude oil 3. Crude oil 1 had a density of 0.8844 g/cm$^3$ and an API of 28.5. Crude oil 1 had the following compositional components by weight percentage, 54.4% saturates, 21.9% aromatics, 18.8% resins, and 4.3% asphaltenes. Crude oil 2 had a density of 0.8574 g/cm$^3$ and an API of 33.5. Crude oil 2 had the following compositional components by weight percentage, 59.1% saturates, 23.0% aromatics, 15.7% resins, and 1.6% asphaltenes. Crude oil 3 had a density of 0.9275 g/cm$^3$ and an API of 40.2. Crude oil 3 had the following compositional components by weight percentage, 40.2% saturates, 27.1% aromatics, 23.9% resins, and 8.5% asphaltenes.

Figure 4A:
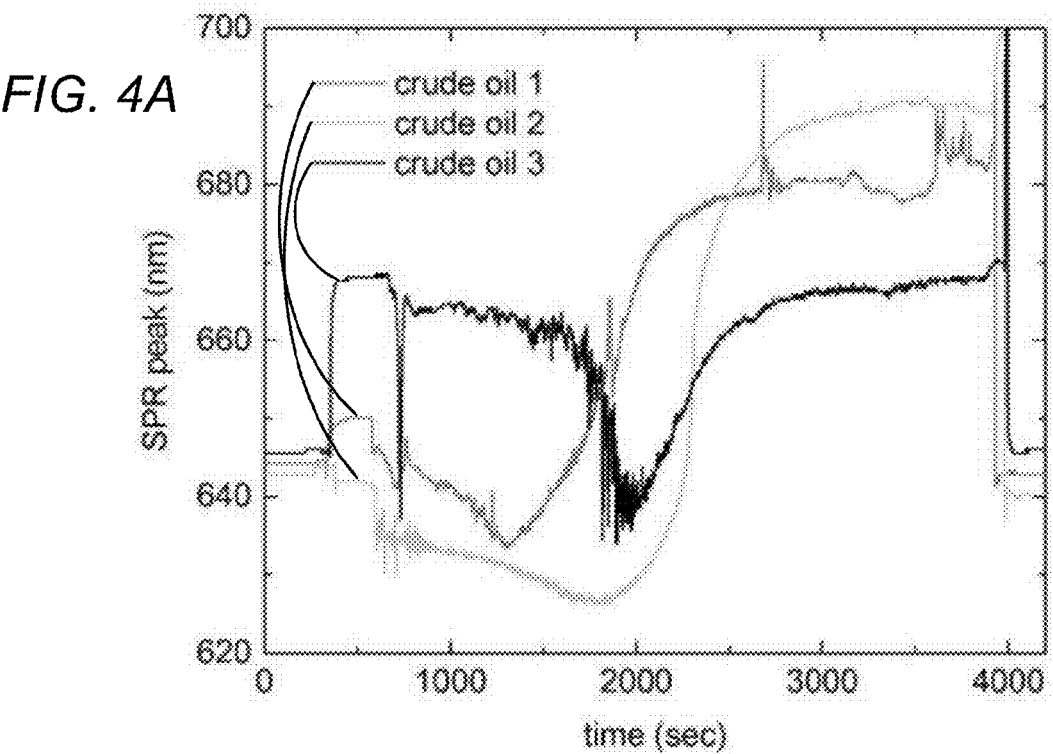
FIG. 4A are plots of SPR weak wavelength over time, which is determined by the SPR sensor of FIG. 1 as part of a ramped titration experiment on three different crude oils.
Figure 4B:
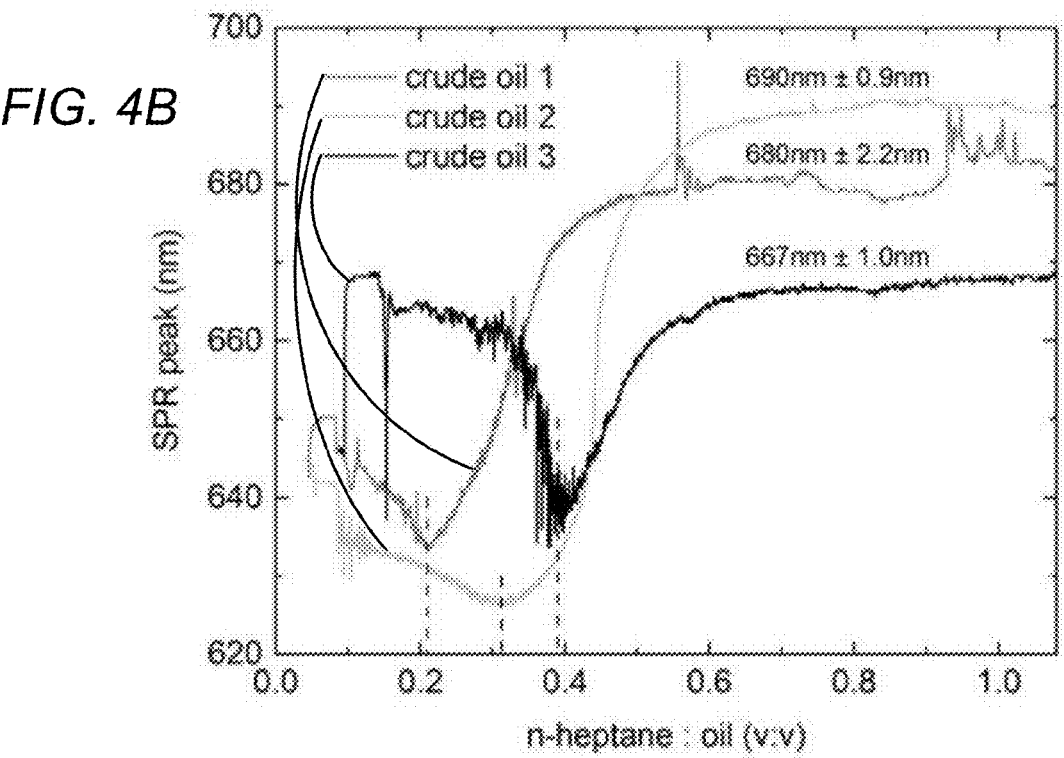
FIG. 4B are plots of SPR weak wavelength versus n-heptane:oil volume fraction, which is determined by the SPR sensor of FIG. 1 as part of the ramped titration experiment on three different crude oils of FIG. 4A.

FIGS. 4A and 4B shows the results from three ramped titration experiments, showing the SPR peak wavelength measured versus time as the n-heptane:oil volume ratios was varied over time, and also versus the n-heptane:oil volume ratio. FIGS. 4A and 4B highlight the ability of the SPR sensor to measure the variation in: asphaltene deposition onset, the rate of deposition, and the density of the final deposit formed. The asphaltene deposition onset volume ratios were 0.202 for crude oil 1, 0.311 for crude oil 2, and 0.390 for crude oil 3. Crude oils 1 and 3 had higher asphaltene contents than crude oil 2, but they deposited more slowly than crude oil 2 after asphaltene deposition. The deposits' density were inversely proportional to the initial crude oil density, which can be determined from the SPR peak wavelength at steady-state and Eqn. 7. The lightest crude oil, crude oil 2 (with a density of 0.857 g/cm$^3$), had a final SPR peak wavelength of 690 nm with an effective refractive index of 1.547, yielding the highest deposit density at 0.995 g/cm$^3$. The heaviest crude oil, crude oil 3 (with a density of 0.928 g/cm$^3$), had a final SPR peak wavelength of 667 nm with an effective refractive index of 1.528 and the least dense deposit at 0.935 g/cm$^3$. The black crude oil, crude oil 1 (with a density of 0.884 g/cm$^3$) was in the middle with a deposit density near 0.970 g/cm$^3$. Since asphaltenes are reported to have densities ranging from 1.1-1.2 g/cm$^3$, it is likely that the deposit was an arrangement of spotted islands or that the layer had entrapped fluid during formation. Both would yield a lower effective deposit density. The inverse relationship between neat crude oil density and deposit density may be the result of a deposition mechanism and/or varying asphaltene compositions.

Figure 5:
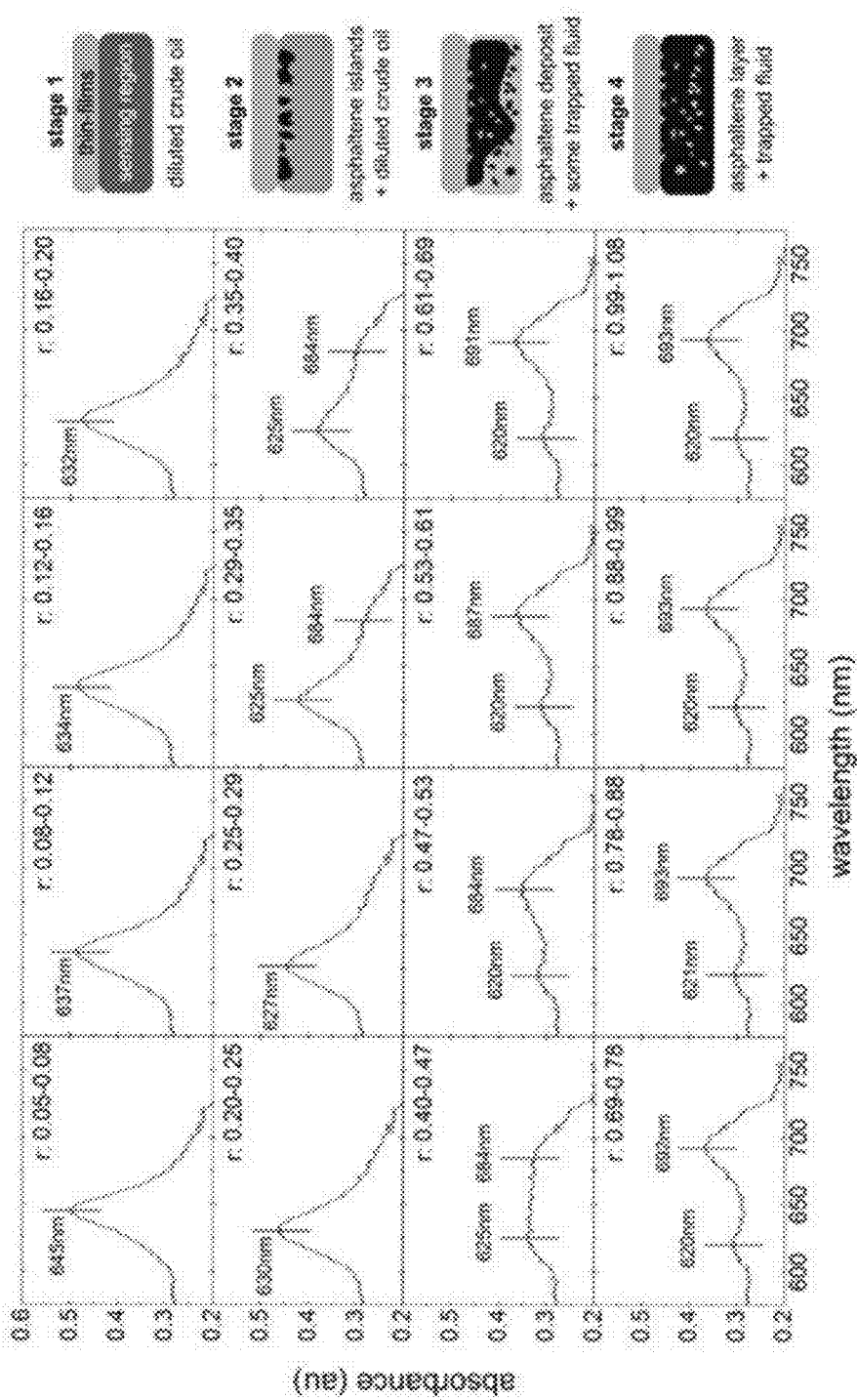
FIG. 5 are plots of exemplary SPR absorbance spectra, which is determined by the SPR sensor of FIG. 1 as part of the titration experiment at various n-heptane:oil volume ratios for a crude oil sample along with schematic diagrams of a proposed asphaltene deposition mechanisms for the four-stages of the titration experiment.

The SPR sensor 101 provides a powerful tool for understanding the mechanisms of asphaltene deposition. The SPR spectral data can be informative by permitting observation of the time-wise formation of the deposit. FIG. 5 shows the measured SPR absorbance spectra spanning different titration ratios for crude oil 2. Below, we provide one possible explanation for the evolution of the SPR spectral data from our titration experiments.

In stage 1, the mixture of crude oil 2 and n-heptane is the primary analyte responsible for the SPR peak wavelength in the sensing region. The top-left panel of FIG. 5 shows an n-heptane:oil ratio of r=0.05-0.08 with a resulting SPR peak wavelength of approximately 645 nm. As the crude oil is further diluted with n-heptane, e.g. ratio of r=0.16-0.20 in the top-right panel, the SPR peak wavelength blue-shifts as expected to approximately 632 nm.

In stage 2, the gradual appearance of a second SPR peak indicates that an initial deposit has formed. The SPR peak wavelength continues to blue-shift to approximately 625 nm until the onset point is reached at r=0.311, at which point the presence of another peak is evident (r=0.29-0.35). This represents the beginning of stage 2, where asphaltenes have started to form spots or islands on the thin-film surface. However, the original SPR peak associated with the fluid mixture continues to blue-shift slightly, down to approximately 620 nm, as the titration ratio is increased. This indicates that in stage 2, both the flowing mixture and the asphaltene deposit are detected in the sensing region.

In stage 3, the asphaltene deposit occupies the majority of the SPR sensing zone. As more asphaltenes deposit on the SPR sensing surface, the deposit's SPR peak grows in amplitude and red-shifts slightly from approximately 684 nm to approximately 691 nm. Conversely, the fluid's SPR peak shrinks and eventually stabilizes without shifting in wavelength. In this stage, the two SPR peaks are present at all times, but the fluid peak is largely static because the fluid is trapped within porous regions of the asphaltene deposit, after r=0.47-0.53.

Finally, in stage 4, the entire SPR sensing zone is occupied with a static hybrid deposit. After r=0.61-0.69, neither the fluid nor the asphaltene deposit SPR peaks have notable shifts in wavelength or changes in amplitude. The proposed 4-stage mechanism explains the evolution of the SPR peak wavelengths under varying titration ratios.

Figure 6:
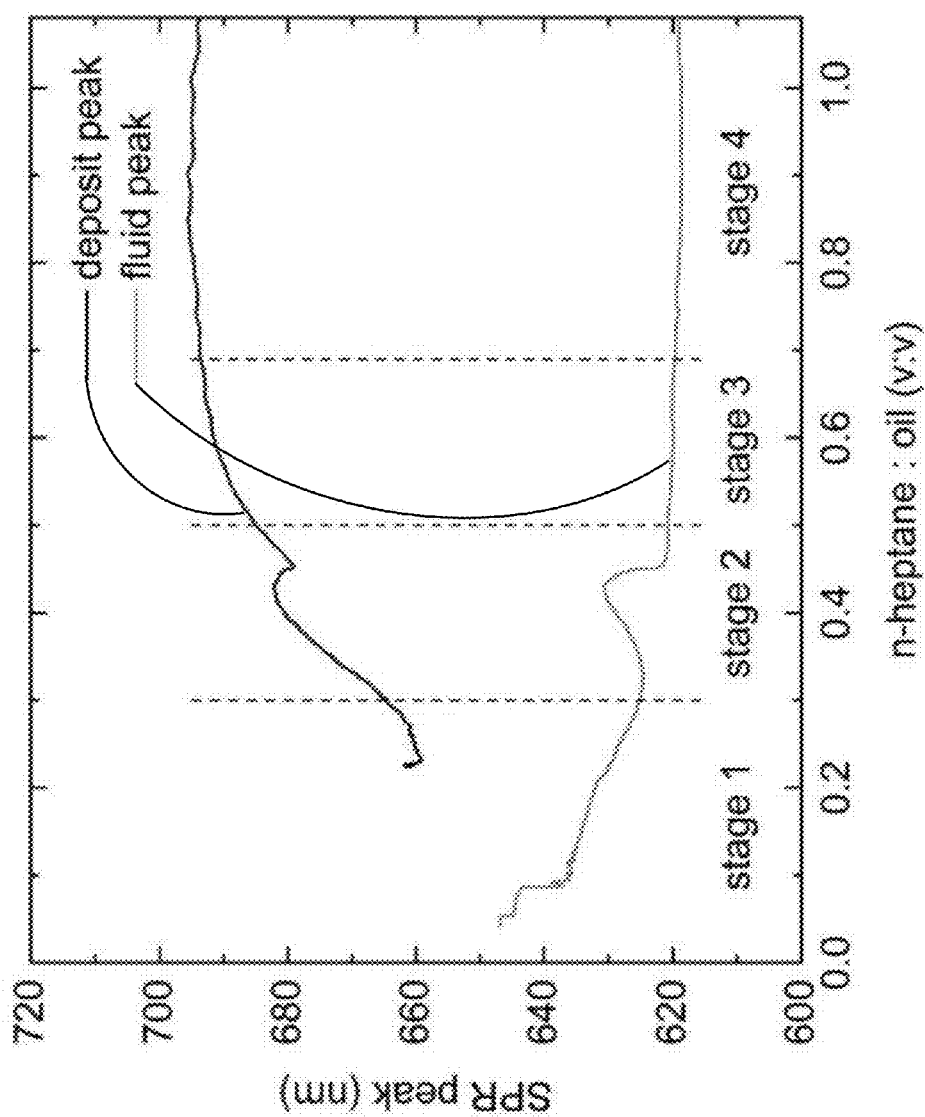
FIG. 6 are plots of SPR peak wavelength versus n-heptane:oil volume fraction for the fluid and the deposit, which is determined by the SPR sensor of FIG. 1 as part of the titration experiment for the crude oil sample of FIG. 5 where the spectral data is analyzed with a two-peak model function.

FIG. 6 summarizes the 4-stages by plotting the SPR peak locations of both the fluid and the deposit for the crude oil 2 data. A Levenberg-Marquadt non-linear least-square fitting approach based on two peaks was performed, where both peaks were modelled with a pseudo-Voigt profile—a linear combination of Gaussian and Lorentzian line profile functions. The momentary rise in stage two is an artefact from fitting, where the spectral data showed a single large-flat-peak in the crossover region from fluid to deposit—as observed in FIG. 5 around a ratio of 0.40. The dynamic SPR sensor data, like that of FIGS. 5 and 6, can inform deposition models by enabling simultaneous observation of both crude oil fluid and the deposit layer during such deposition events.

The experiments described herein show that the operation of the SPR sensor is robust in measuring asphaltene depositions when exposed to unprocessed crude oil samples that were titrated with a precipitant. More specifically, the operations of the SPR sensor can directly quantifies asphaltene deposition onset. Shifts in the SPR peak wavelength can be used to determine the onset and deposition of asphaltenes from titration experiments. A model of the SPR sensor can be tuned or calibrated and used to relate SPR peak wavelength to an effective refractive index of the crude oil, which can be then related to an estimate of deposit density. The ability to simultaneously measure both the fluid's refractive index/density and the solid deposit's refractive index/density, can enable real-time measurement of asphaltene/organic deposition under live conditions. Therefore, the SPR sensor can enable direct feedback for flow assurance workflows, monitoring stability for operations like solvent dilution, sample depressurization.

The SPR sensor 101 can also be used to quantify the phase behavior of hydrocarbon fluids based on a step change in the SPR peak wavelength, which can include one or more of the following applications:

Detection of bubble point; the formation of vapor (may be also dissolution) from a hydrocarbon fluid induced by temperature and pressure changes. The SPR sensor can be used to detect either the vapor or liquid phases.

Detection of liquid condensation; the formation of a liquid film on the sensor surface from hydrocarbon vapors induced by temperature or pressure changes.

Detection of hydrate formation induced by temperature or pressure changes.

Detection of scaling or inorganic precipitation induced by composition, temperature or pressure changes.

Detection of asphaltene onset; the formation of asphaltenes aggregates in the hydrocarbon fluid induced by temperature, pressure or composition changes. The SPR sensor can be used to detect either the liquid phase (maltenes) or a precipitated/deposited solid phase (asphaltenes).

Sample fluid typing by means of measuring the direction and/or magnitude of the SPR shift when undergoing phase change.

In another aspect, a compact and robust SPR probe sensor is provided that can be used to quantify the phase behavior of hydrocarbon fluids in ruggedized applications, such as part of a downhole tool that experiences high pressure high temperature conditions of a downhole wellbore environment or as part of a surface-located system at a wellsite or pipeline. Similar to the SPR sensor of FIG. 1, the SPR probe sensor is based on a surface-sensitive optical phenomenon known as surface plasmon resonance, or SPR. Surface plasmon resonance describes a condition in which light incident onto a highly conductive metallic film couples into resonant charge oscillations of the metal, resulting in light that is effectively "glued" to the surface of the film. In this trapped state, light is highly sensitive to slight perturbations in the dielectric environment in the immediate vicinity of the film (less than 1 µm away). This property is useful for quantifying the phase behavior of hydrocarbon fluids based on a step change in the SPR peak wavelength, which can include one or more of the following applications:

Detection of bubble point; the formation of vapor (may be also dissolution) from a hydrocarbon fluid induced by temperature and pressure changes. The SPR sensor probe can be used to detect either the vapor or liquid phases.

Detection of liquid condensation; the formation of a liquid film on the sensor surface from hydrocarbon vapors induced by temperature or pressure changes.

Detection of hydrate formation induced by temperature or pressure changes.

Detection of scaling or inorganic precipitation induced by composition, temperature or pressure changes.

Detection of asphaltene onset; the formation of asphaltenes aggregates in the hydrocarbon fluid induced by temperature, pressure or composition changes. The SPR sensor probe can be used to detect either the liquid phase (maltenes) or a precipitated/deposited solid phase (asphaltenes).

Sample fluid typing by means of measuring the direction and/or magnitude of the SPR shift when undergoing phase change.

The SPR probe sensor embodiments as described herein can be more amendable to the downhole high-pressure high temperature environment than other methods, as the optical components of the SPR probe sensor are self-aligned, the system requires no motorized parts, and the spectroscopic technique readily integrates with existing downhole tools.

Figure 15:
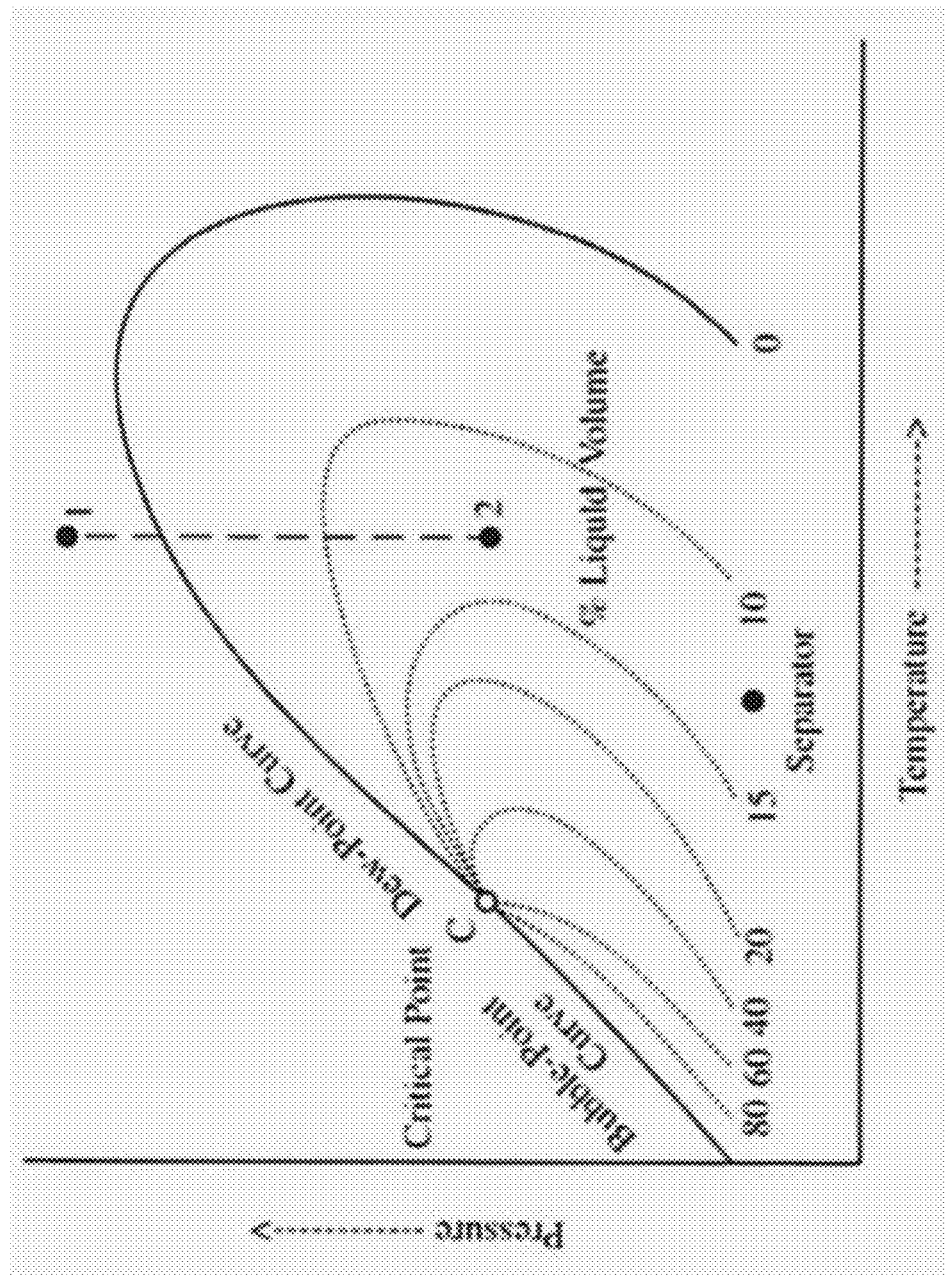
FIG. 15 is a phase diagram of a gas condensate, showing phase boundaries and conditions under which multiple phases can coexist at equilibrium.

Note that a phase transition in a hydrocarbon reservoir fluid can occur as the pressure and temperature of the fluid deviates from reservoir conditions. Retrograde condensates are one type of hydrocarbon fluid that exhibit a dewpoint (formation of a liquid phase from a gas phase) during isothermal depressurization at the temperature of interest. Presence of the liquid phase depends on temperature and pressure conditions in the reservoir allowing condensation of liquid from vapor. FIG. 15 shows the phase diagram of a typical gas condensate. The fluid is in gaseous form at pressures above the solid curve, while it forms liquid condensate once the pressure drops below the solid curve. Point 1 in FIG. 15 represents the gaseous state of the system at a given temperature. As the pressure drops at constant temperature, the system crosses the dew point curve (solid curve) and liquid phase forms (phase transition from gas-to-liquid). Point 2 in FIG. 15 depicts the two-phase state of the system. Formation of liquid phase in the pores during production of a gas field results in reduced liquid recovery. Condensate dropout near the wellbore can significantly reduce the productivity index of the well. In severe cases the well can prematurely die decreasing overall recovery under naturally flowing conditions. Therefore, it is imperative to measure the dew point as well as liquid drop-out of such hydrocarbon fluids at reservoir condition and plan the production accordingly.

Phase behavior studies of lean gas condensates are of growing importance in reservoir fluid analysis. Saturation pressure (psat) or the dew point of a gas condensate is an important thermo-physical property of such fluids. However, measurement of the dew point is usually difficult to perform in conventional Pressure-Volume-Temperature (PVT) systems. The complications stem from the difficulty in detecting and quantifying very small volumes of liquid in the gas. The dew point measurement becomes increasingly difficult as the liquid content of the gas reduces. Dead volumes in conventional PVT cells limit the minimum measurable liquid volumes. The minimum liquid volume fraction is a function of cell geometry. Conventional methods using PVT cells run into major difficulties when it comes to measuring the dew point of fluids with small volume liquid content (e.g., lean condensate). There have been attempts to increase the cell volume (e.g., 205 cc in Sanchez Gas 250-1000 cell) to increase the amount of liquid collected at and below dew point pressure. However, the increase in accuracy comes at the cost of significantly larger sample volume and operational difficulty. Furthermore, conventional techniques suffer from poor repeatability, reproducibility, and accuracy.

Hence, there is a strong demand for a reliable, accurate and highly sensitive technique for dew point and phase volume measurement.

In another example, the determination of asphaltene onset conditions and also the amount of asphaltene precipitation under varying conditions are essential measurements for both upstream and downstream operations. It is useful to characterize asphaltene behavior to optimize flow assurance and to prevent adverse asphaltene drop out during production and processing of the oil. Asphaltenes can deposit in reservoirs, wellbore tubing, flow-lines, separators, etc. The deposits can interrupt and potentially stop production due to the formation of plugs. The first step in the deposition process is flocculation (aggregation) of molecules. During production, the solubility of the asphaltenes in the crude oil decreases as the pressure decreases as the fluid travels through the reservoir and the well bore. The asphaltene onset pressure (AOP) is the pressure at which asphaltenes first begin to precipitate at a fixed temperature. Asphaltene deposition can begin deep in the wellbore while the pressure is well above the bubble point. Asphaltenes can also precipitate during miscible flooding with $CO_2$ and natural gases as well as due to comingling of different fluids.

In accordance with some example embodiments, a method and apparatus are provided for measuring hydrocarbon phase transitions, namely dew point, bubble point and asphaltene onset pressure (AOP) at HPHT conditions and downhole. The method utilizes surface plasmon resonance to measure the refractive index shifts of reservoir fluids when phase transitions are induced by pressure, temperature, or composition changes.

Some example embodiments involve the design and experimental workflow of an SPR probe sensor that can operate under high pressure and high temperature conditions. In an example implementation, the instrument includes two parts: the SPR sensor probe and optionally a sample handling system for temperature and pressure control/monitoring. The SPR sensor probe may be constructed from an optical fiber (e.g., a sapphire optical fiber). In some examples, one end of a fiber optic core can be coated with a thin film of metal (e.g. gold, silver) and a thin film of dielectric protection (e.g., zirconium oxide). The SPR sensor probe can be excited using a polychromatic light source (e.g., a broadband tungsten-halogen light source) providing light from 400-2400 nm, although other wavelengths may be suitable as per application. The SPR coupling at the interface of the thin film of metal is imprinted onto the spectra of the light reflected from the SPR sensor probe or light transmitted by the SPR sensor probe, which is measured by a spectrometer. The spectra of the reflected or transmitted light as measured by the spectrometer can be analyzed to determine an SPR peak wavelength. An abrupt change or shift in the SPR peak wavelength can be used to detect phase change of complex multi-component reservoir fluids in order to measure bubble point, dew point, asphaltene onset or other relevant phase transitions. The phase change can occur due to environmental conditions or can be induced by the sample handling system.

FIGS. 7A to 7E illustrate example embodiments of a reflective-type SPR sensor probe 710 where the SPR coupling at the interface of a thin film of metal is imprinted onto the spectra of the light reflected from the SPR sensor probe 710, which is measured by a spectrometer 702. The SPR sensor probe 710 is part of a system 700 which includes four sub-components: a polychromatic light source 701, a four-port fiber splitter 705, a flow line 709 with the SPR sensor probe 710 integral to the flow line 709, and a spectrometer 702. The polychromatic light source 701 can be a tungsten halogen light supplying polychromatic radiation at wavelengths from 400-2400 nm, although other wavelengths or light source types may be used as per application. The polychromatic light generated by the light source 701 is directed into port 1 (labeled 703) of the fiber splitter 705. The fiber splitter 705 transmits part of the supplied polychromatic light to port 3 (labeled 707) of the fiber splitter 705, where it is coupled to the fiber optic core of the SPR sensor probe 710. The light that is supplied to the fiber optic core of the SPR sensor probe 710 can undergo multiple total internal reflections within the SPR sensor probe 710. Each reflection may result in a loss of light intensity due to SPR coupling where the light couples to or excites surface plasmon oscillations at the interface of thin metal film and the hydrocarbon fluid that flows through the flow line 709. The SPR sensor probe 710 includes a mirror that reflects light backward toward port 103 (labeled 707) of the fiber splitter 705. This reflected light traverses the length of the SPR sensor probe 710 length once more, potentially losing additional light intensity due to SPR coupling. Part of the reflected light (with losses due to the SPR coupling) is transmitted by the fiber splitter 705 from port 103 (labeled 707) to port 102 (labeled 704) of the fiber splitter 705 for supply to the spectrometer 702. The spectrometer 702 measures the spectra of the reflected light (which represents the intensity of the reflected light over a number of different wavelengths). The fiber splitter 705 can also direct part of the polychromatic light generated by the light source 701 via port 4 (labeled 706) to an optional spectrometer 708. The spectrometer 708 can measure the spectra of the polychromatic light (which represents the intensity of the polychromatic light with over a number of different wavelengths, with no losses due to SPR coupling). This provides a reference spectrum and enables correction for noise and long-term drift and also allows normalization of the losses experienced due to the SPR coupling. In accordance with some examples, the system 700 can be designed to withstand downhole high-pressure high temperature environmental conditions in a wellbore that traverses a subterranean formation.

Figure 7A:
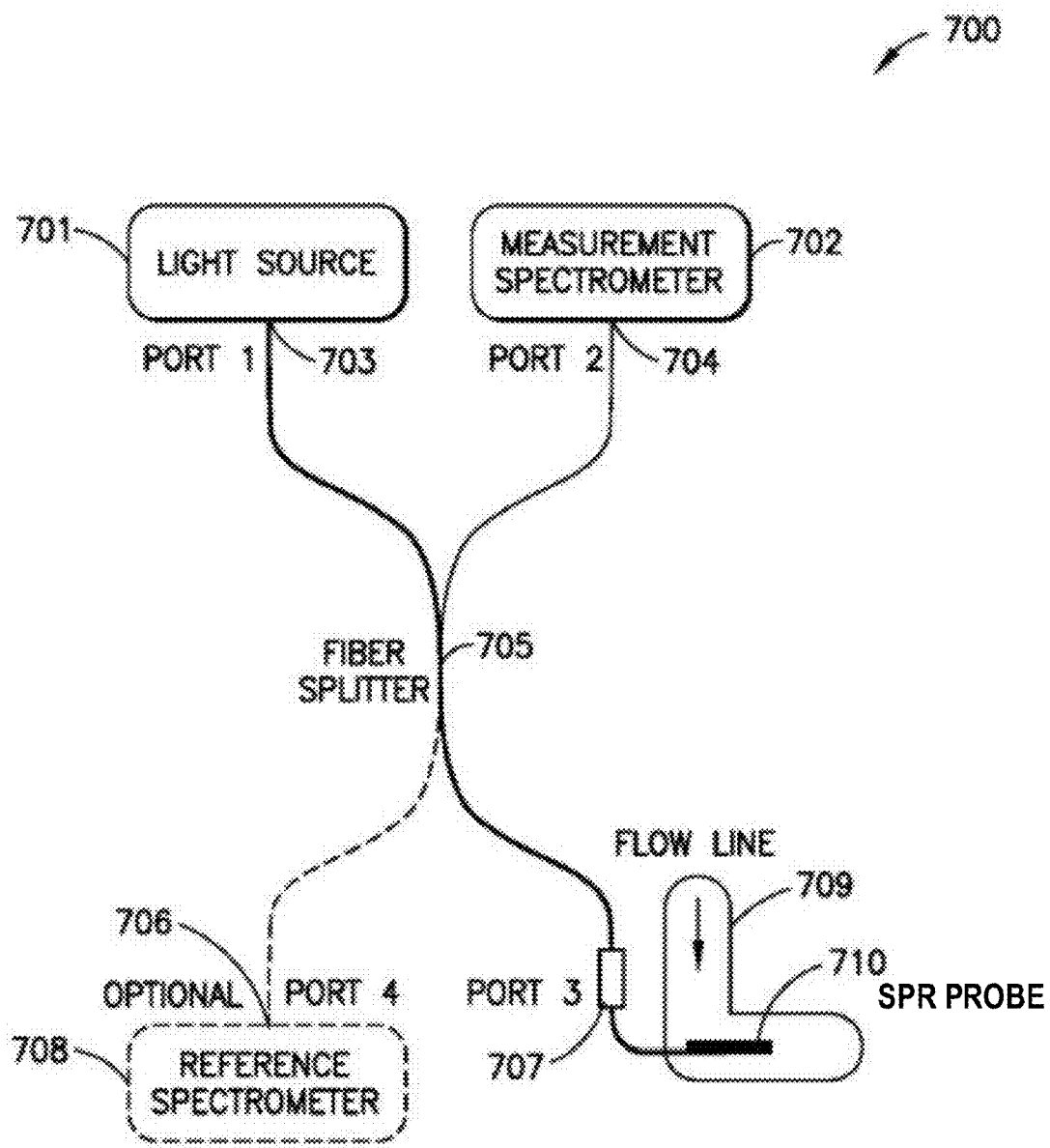
FIGS. 7A to 7E illustrate example embodiments that employ a reflective-type SPR sensor probe.
Figure 7B:
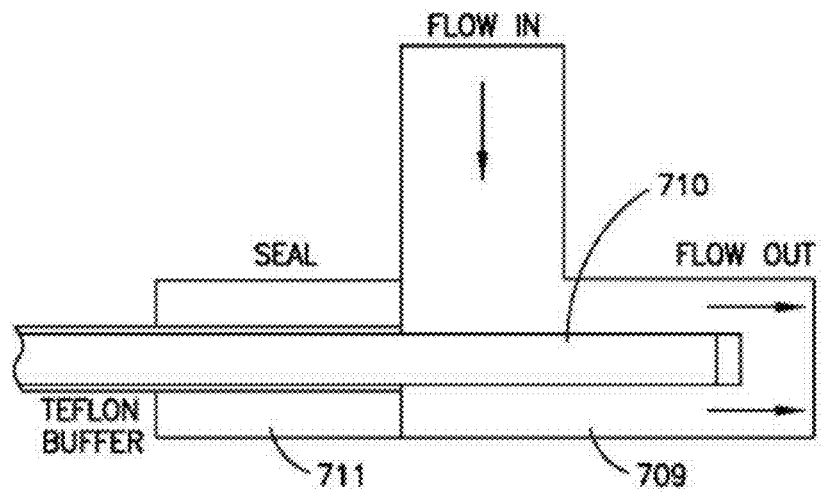
Figure 7C:
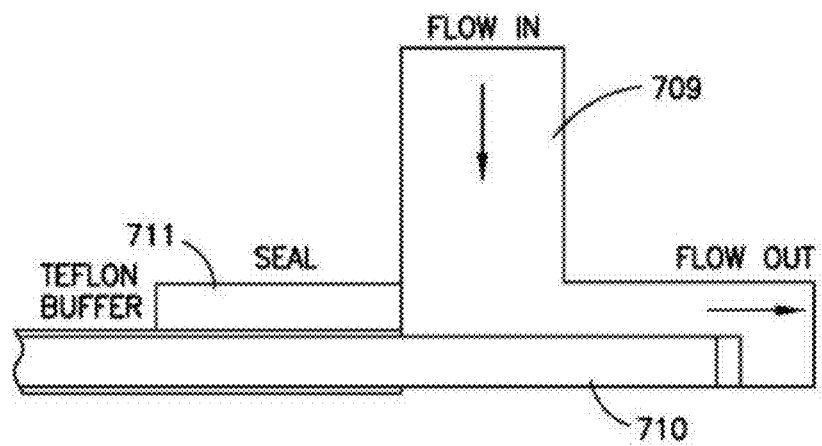
Figure 7D:
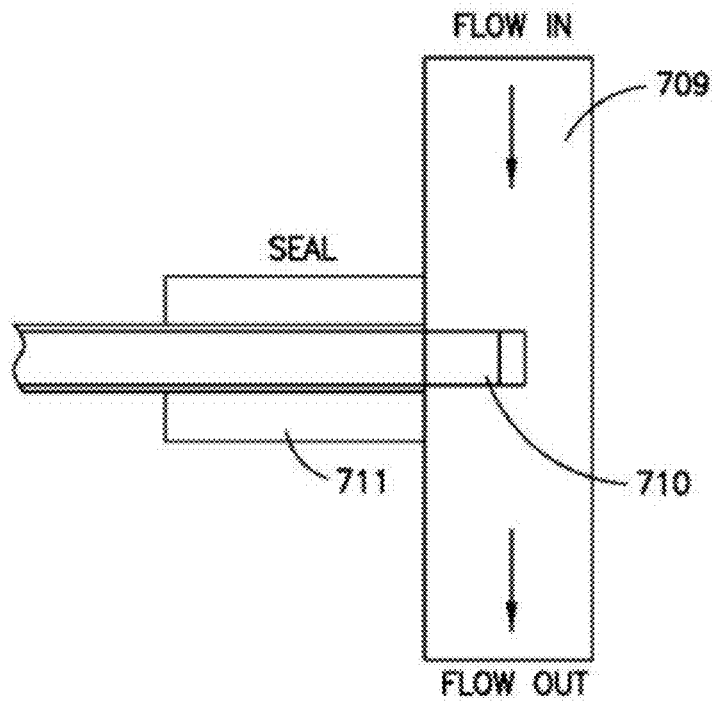

FIGS. 7B, 7C and 7D show three different configurations for the flow line 709 of FIG. 7A. It should be understood that any suitable flow line configuration and/or geometry may be provided and those shown are illustrative examples. More specifically, the configuration of the flow line 709 of FIGS. 7B and 7C employ flow paths that are elbows, or 90-degree bends. In the configuration of FIG. 7B, the SPR sensor probe 710 is disposed approximately along the center of the flow path. In the configuration of FIG. 7C, the SPR sensor probe 710 is disposed adjacent one of the walls of the flow line 709. In both configurations, the part of the flow line 709 occupied by the SPR sensor probe 710 is analogous the flow cell and associated SPR sensing zone of the SPR sensor of FIG. 1. In both configurations, a buffer and seal 711 is provided which allow the SPR sensor probe 710 to extend into the flow region of the flow line 709 in a fluid-tight manner to prevent the sample fluid from exiting the flow line 709 via the entrance point of the SPR sensor probe 710. The flow region of the FIG. 7D illustrates a configuration of the flow line 709 that employs a straight flow path, and the SPR sensor probe 710 extends transversely relative the flow path into the flow path of the flow line. In this manner, the part of the flow line 709 occupied by the SPR sensor probe 710 is analogous the flow cell and associated SPR sensing zone of the SPR sensor of FIG. 1. In this configuration, a buffer and seal 711 is provided which allow the SPR sensor probe 710 to extend into the flow region of flow line 709 in a fluid-tight manner to prevent the sample fluid from exiting the flow line 709 via the entrance point of the SPR sensor probe 710.

Figure 7E:
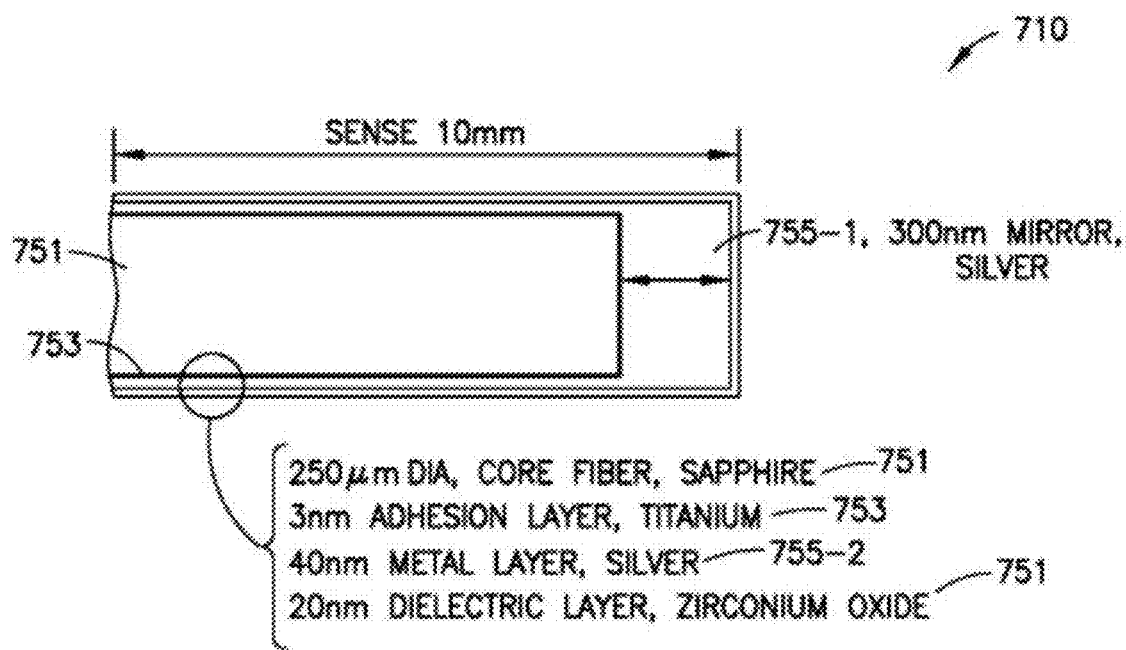

FIG. 7E shows an enlarged cross-sectional view of a sensing portion of the SPR sensor probe 710 of FIG. 7A to 7D. This sensing portion extends into the flow region of the flow line 709 such that it interacts with the sample fluid flowing through the flow line 709. The sensing portion includes a fiber optic core 751, which can be realized from sapphire with a diameter of 250 μm in this example. An adhesion layer 753 of titanium or other suitable material, which can have a thickness of 3 nm, can be used to bond the fiber optic core 751 to metal layer 755 (in this example, a layer of silver). The metal layer portion 755-1 adjacent the end of the fiber optic core 751 is relatively thick (for example, on the order or 300 nm) as compared to the metal layer portion 755-2 that extends adjacent the lengthwise portion of the fiber optic core 751 (which has a thickness, for example, on the order or 40 nm). The thick metal layer portion 755-1 forms a mirror adjacent the end of the fiber optic core 751. A protective (dielectric) layer 757 of zirconium oxide or other suitable dielectric material coats both the thick metal layer portion 755-1 and the thin metal layer portion 755-2.

Interaction of the sample fluid flowing through the flow line 709 on SPR coupling of light reflected by the metal layer portions 755-1 and/or 755-2 of the SPR sensor probe 710 can be used in accordance with the SPR principles described herein to analyze the sample fluid. More specifically, a programmed computing system (similar to the computing system 123 of FIG. 1) can be configured to acquire the spectra of the reflected light as measured by the spectrometer 702 and the spectra of the polychromatic light as measured by the spectrometer 708. It can also perform data storage and analysis of such spectra to determine an SPR peak wavelength at any given point in time as well as variations in SPR peak wavelength over time. In embodiment(s), the SPR peak wavelength can be extracted from the spectra of the reflected light as measured by the spectrometer 702 and the spectra of the polychromatic light as measured by the spectrometer 708 in two steps. First, an absorbance spectrum can be calculated by dividing a characteristic spectrum of the measured spectra (which can be determined by averaging the p-measured spectra per wavelength as measured by the spectrometer 702 over a given measurement time interval) by a characteristic spectrum of the polychromatic light as measured by the spectrometer 708 (which can be determined by averaging the spectra per wavelength as measured by the spectrometer 708 over the same measurement time interval). Note that polychromatic light measured by the spectrometer 708 does not under SPR coupling that is influenced by the sample fluid flowing through the flow line 709. Therefore, the polychromatic light measured by the spectrometer 708 does not experience SPR losses and provides a reference spectrum. Second, a peak detection algorithm is used to determine the SPR peak wavelength from the absorbance spectrum. The SPR peak wavelength can be plotted versus time to observe the evolution of the SPR peak wavelengths to detect phase change of the sample fluid flowing through the flow line 709. The phase change can occur due to environmental conditions or can be induced by a sample handling system. Such analysis can be used to measure bubble point, dew point, asphaltene onset or other relevant phase transitions. Furthermore, a calibrated model similar to the model used to represent the SPR sensor of FIG. 1 can be used to convert the SPR peak wavelength(s) into an effective refractive index for interpretation.

Figure 8A:
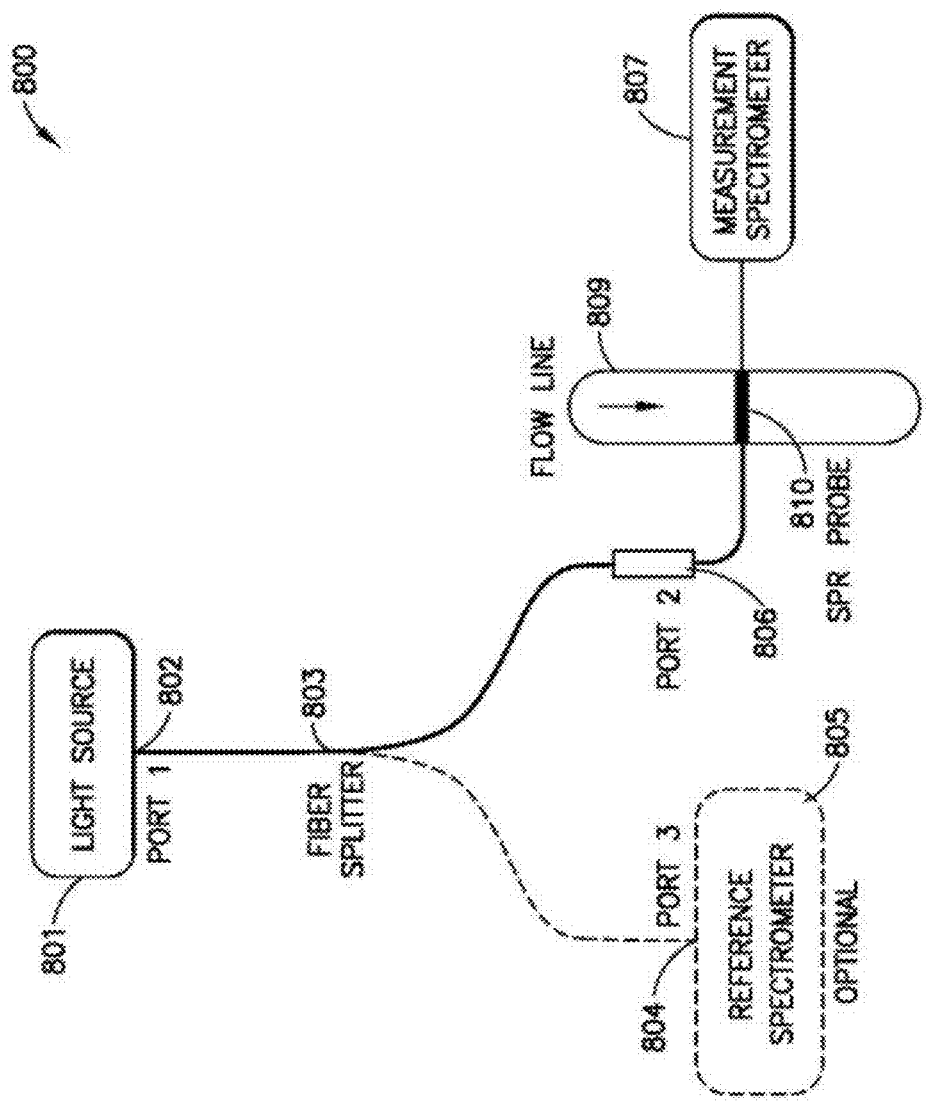
FIGS. 8A to 8C illustrate example embodiments that employ a transmissive-type SPR sensor probe.
Figure 8B:
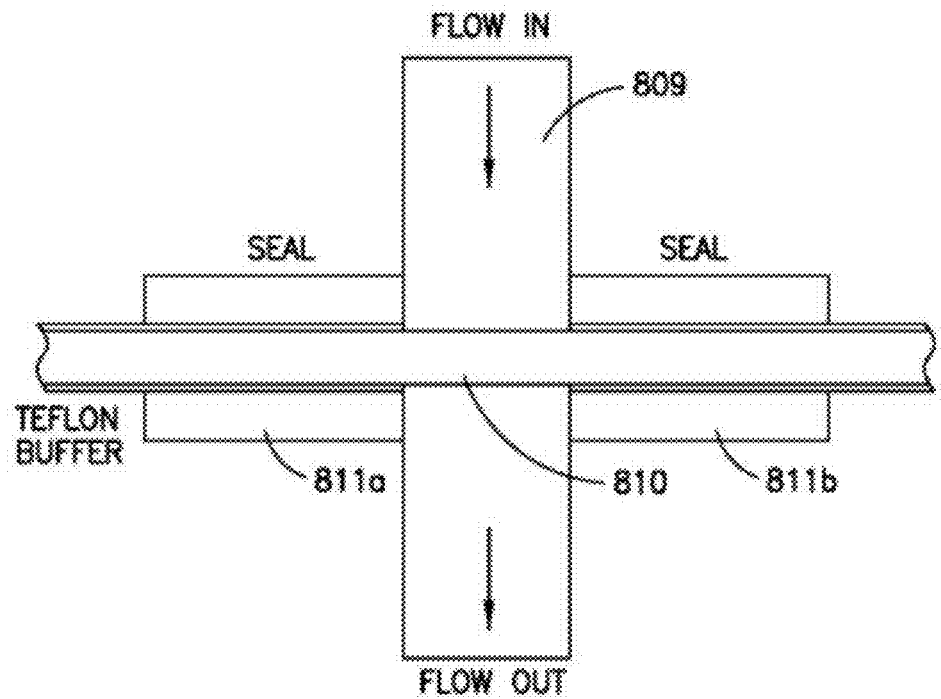
Figure 8C:
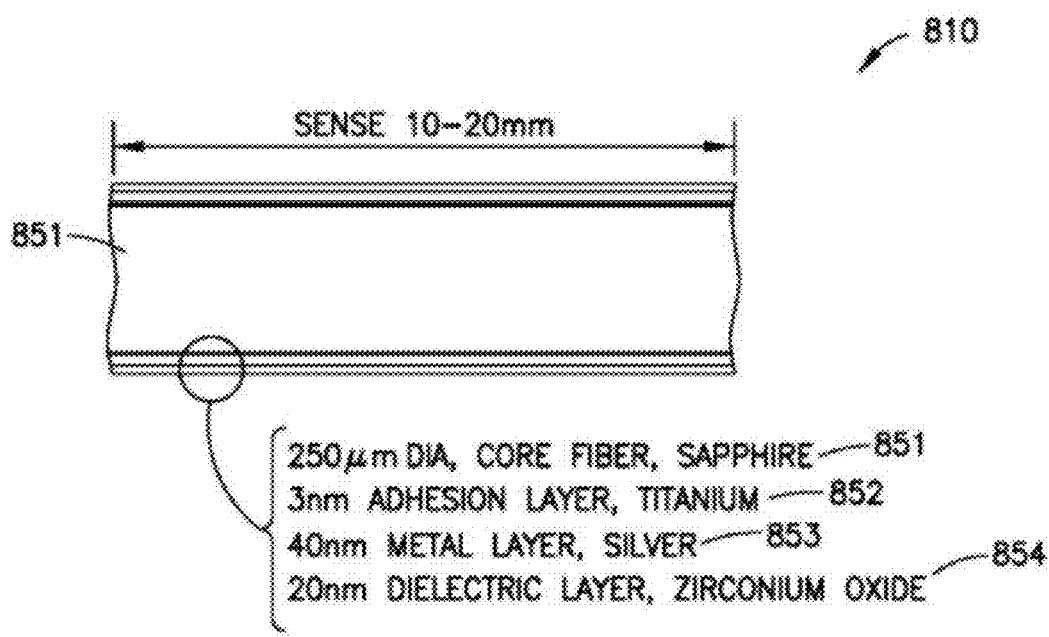

FIGS. 8A to 8C illustrate example embodiments of a transmissive-type SPR sensor probe 810 where the SPR coupling at the interface of a thin film of metal is imprinted onto the spectra of the light transmitted by the SPR sensor probe 810, which is measured by a spectrometer 807. The SPR sensor probe 810 is part of a system 800 which includes four sub-components: a polychromatic light source 801, a four-port fiber splitter 805, a flow line 809 with the SPR sensor probe 810 integral to the flow line 809, and a spectrometer 807. The polychromatic light source 801 can be a tungsten halogen light supplying polychromatic radiation at wavelengths from 400-2400 nm, although other wavelengths or light source types may be used as per application. The polychromatic light generated by the light source 801 is directed into port 1 (labeled 802) of the fiber splitter 803. The fiber splitter 803 transmits part of the supplied polychromatic light to port 2 (labeled 806) of the fiber splitter 803, where it is coupled to one end of the fiber optic core of the SPR sensor probe 810. The light that is supplied to the fiber optic core of the SPR sensor probe 810 can undergo multiple total internal reflections within the SPR sensor probe 810. Each reflection may result in a loss of light intensity due to SPR coupling where the light couples to or excites surface plasmon oscillations at the interface of thin metal film and the hydrocarbon fluid that flows through the flow line 809. The opposite end of the fiber optic core of the SPR sensor probe 710 couples the resultant light (which reflects the loss of light intensity due to SPR coupling) to the spectrometer 807. The spectrometer 807 measures the spectra of the transmitted light (which represents the intensity of the transmitted light over a number of different wavelengths). The fiber splitter 803 can also direct part of the polychromatic light generated by the light source 801 via port 3 (labeled 804) to an optional spectrometer 805. The spectrometer 805 can measure the spectra of the polychromatic light (which represents the intensity of the polychromatic light with over a number of different wavelengths, with no losses due to SPR coupling). This provides a reference spectrum and enables correction for noise and long-term drift and also allows normalization of the losses experienced due to the SPR coupling. In accordance with some examples, the system 800 can be designed to withstand downhole high-pressure high temperature environmental conditions in a wellbore that traverses a subterranean formation.

FIG. 8B illustrates a configuration of the flow line 809 that employs a straight flow path, and the SPR sensor probe 810 extends transversely relative the flow path into the flow path. It should be understood that any suitable flow line configuration and/or geometry may be provided and those shown are illustrative examples. In the configuration of FIG. 8B, a buffer and seal 811a is provided which allow the SPR sensor probe 810 to extend into the flow region of flow line 809 in a fluid-tight manner to prevent the sample fluid from exiting the flow line 809 via the entrance point of the SPR sensor probe 810.

FIG. 8C shows an enlarged cross-sectional view of a sensing portion of the SPR sensor probe 810 of FIGS. 8A and 8B. This sensing portion extends into the flow region of the flow line 809 such that it interacts with the sample fluid flowing through the flow line 809. The sensing portion includes a fiber optic core 851, which can be realized from sapphire with a diameter of 250 μm in this example. An adhesion layer 852 of titanium or other suitable material, which can have a thickness of 3 nm, can be used to bond the fiber optic core 851 to a metal layer 853 that extends along the lengthwise extent of the sensing portion. The metal layer 853 can be realized from silver with a thickness of 40 nm in this example. A protective (dielectric) layer 854 of zirconium oxide or other suitable dielectric material coats the metal layer 853 that extends along the lengthwise extent of the sensing portion.

Interaction of the sample fluid flowing through the flow line 809 on SPR coupling of light transmitted by the SPR sensor probe 810 can be used in accordance with the SPR principles described herein to analyze the sample fluid. More specifically, a programmed computing system (similar to the computing system 123 of FIG. 1) can be configured to acquire the spectra of the transmitted light as measured by the spectrometer 807 and the spectra of the polychromatic light as measured by the spectrometer 805. It can also perform data storage and analysis of such spectra to determine an SPR peak wavelength at any given point in time as well as variations in SPR peak wavelength over time. In embodiment(s), the SPR peak wavelength can be extracted from the spectra of the transmitted light as measured by the spectrometer 807 and the spectra of the polychromatic light as measured by the spectrometer 805 in two steps. First, an absorbance spectrum can be calculated by dividing a characteristic spectrum of the measured spectra (which can be determined by averaging the measured spectra per wavelength as measured by the spectrometer 807 over a given measurement time interval) by a characteristic spectrum of the polychromatic light as measured by the spectrometer 805 (which can be determined by averaging the spectra per wavelength as measured by the spectrometer 805 over the same measurement time interval). Note that polychromatic light measured by the spectrometer 805 does not under SPR coupling that is influenced by the sample fluid flowing through the flow line 809. Therefore, the polychromatic light measured by the spectrometer 805 does not experience SPR losses and provides a reference spectrum. Second, a peak detection algorithm is used to determine the SPR peak wavelength from the absorbance spectrum. The SPR peak wavelength can be plotted versus time to observe the evolution of the SPR peak wavelengths to detect phase change of the sample fluid flowing through the flow line 809. The phase change can occur due to environmental conditions or can be induced by a sample handling system. Such analysis can be used to measure bubble point, dew point, asphaltene onset or other relevant phase transitions. Furthermore, a calibrated model similar to the model used to represent the SPR sensor of FIG. 1 can be used to convert the SPR peak wavelength(s) into an effective refractive index for interpretation.

Note that the fiber optic core 751 or 851 can be made of materials other than those specified herein, as long as the material has a higher refractive index than that of the fluid sample and supports the spectrum of light propagation. Also note that the spectrometers 702, 708, 807, 805 (or other spectrometers described herein) can be based on spectrally dispersive technologies or on discrete photodiodes and filters.

In alternate embodiments, the SPR sensing system 700 or 800 as described herein can be used to perform one or more titration experiments to measure asphaltene deposition onset. The titration experiment varies the volume ratio of n-heptane (or some other asphaltene precipitant) relative to the crude oil of interest in order to measure the onset of asphaltene deposition.

Figure 9:
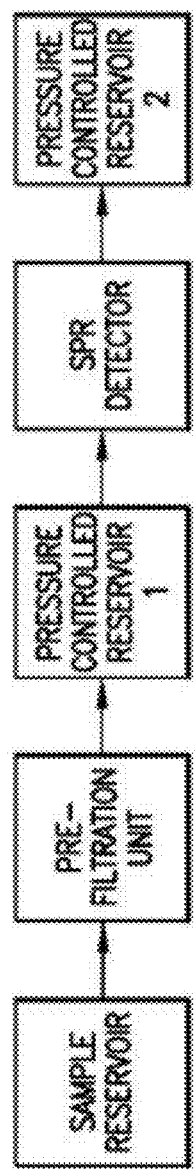
FIG. 9 shows a fluid analysis platform using an SPR sensor probe (labeled "SPR detector) and associated sample handling, pressure and temperature control system, which employs preset isothermal conditions for all blocks.
Figure 10:
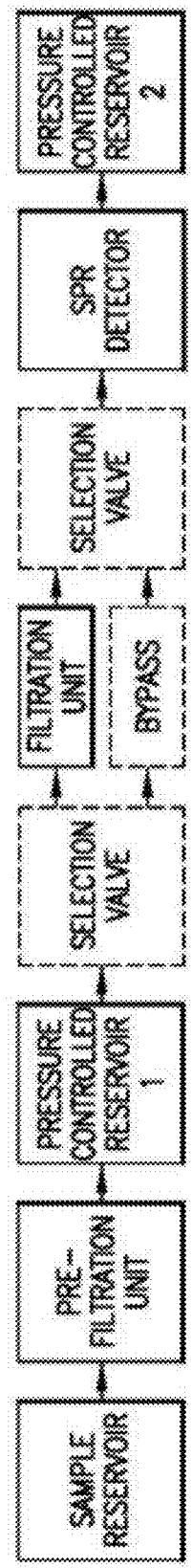
FIG. 10 shows a fluid analysis platform using an SPR sensor probe (labeled "SPR detector) and associated sample handling, pressure and temperature control system, which employs filtration and isothermal conditions for all blocks.

FIGS. 9 and 10 show exemplary sample handling elements that can be utilized to measure phase transitions using the SPR sensing system 700 or 800 as described herein. The simplest configuration is that shown in FIG. 9. Here, the sample reservoir is sub-sampled via a pre-filtration unit into pressure controlled reservoir 1. The flow cell of the respective SPR sensing system 700 or 800 as described herein (labeled SPR detector in FIG. 9) bridges the pressure controlled reservoir 1 and pressure controlled reservoir 2. All of the fluid handling elements can be maintained at isothermal conditions preset by the user. The isothermal conditions can be maintained by closed loop control of a thermoelectric-based heater/cooler apparatus (or other temperature control system) that is thermally coupled to these fluid handling elements (including the pressure controlled reservoir 1, flow cell and pressure controlled reservoir 2) such that the fluid temperature of these fluid handling elements is maintained at the isothermal conditions preset by the user. Fluid(s) can be flowed through the flow line at varying pressures by controlling the pressure differential between reservoir 1 and reservoir 2, while simultaneously recording the SPR spectra at each pressure condition. A phase transition will be detected by an abrupt change in the SPR peak wavelength measured by the SPR sensing system. Furthermore, the user can vary the isothermal conditions of the fluid handling elements of the system as desired.

FIG. 10 shows a more advanced sample handling elements that permits filtration and removal of solids for the sample under investigation. Filtration can remove solid particles like asphaltenes that may foul the SPR probe surface over extended use. Filtration would also permit more robust phase transition detection by physically removing solid particles from the bulk sample fluid. In another embodiment, an inline mixer can be added in the fluid flow path between the pressure controlled reservoir 1 and the SPR detector to ensure the sample is well-mixed. The use of an active or passive mixer can enhance phase transition in the well-mixed sample. Note that all of the fluid handling elements can be maintained at predefined isothermal conditions. The isothermal conditions can be maintained by closed loop control of a thermoelectric-based heater/cooler apparatus (or other temperature control system) that is thermally coupled to these elements such that the fluid temperature of these elements is maintained at the predefined isothermal conditions. Fluid(s) can be flowed through the flow line at varying pressures by controlling the pressure differential between reservoir 1 and reservoir 2, while simultaneously recording the SPR spectra at each pressure condition. A phase transition will be detected by an abrupt change in the SPR peak wavelength measured by the SPR sensing system. Furthermore, the isothermal conditions of the fluid handling elements of the system can be varied as desired.

Figure 11:
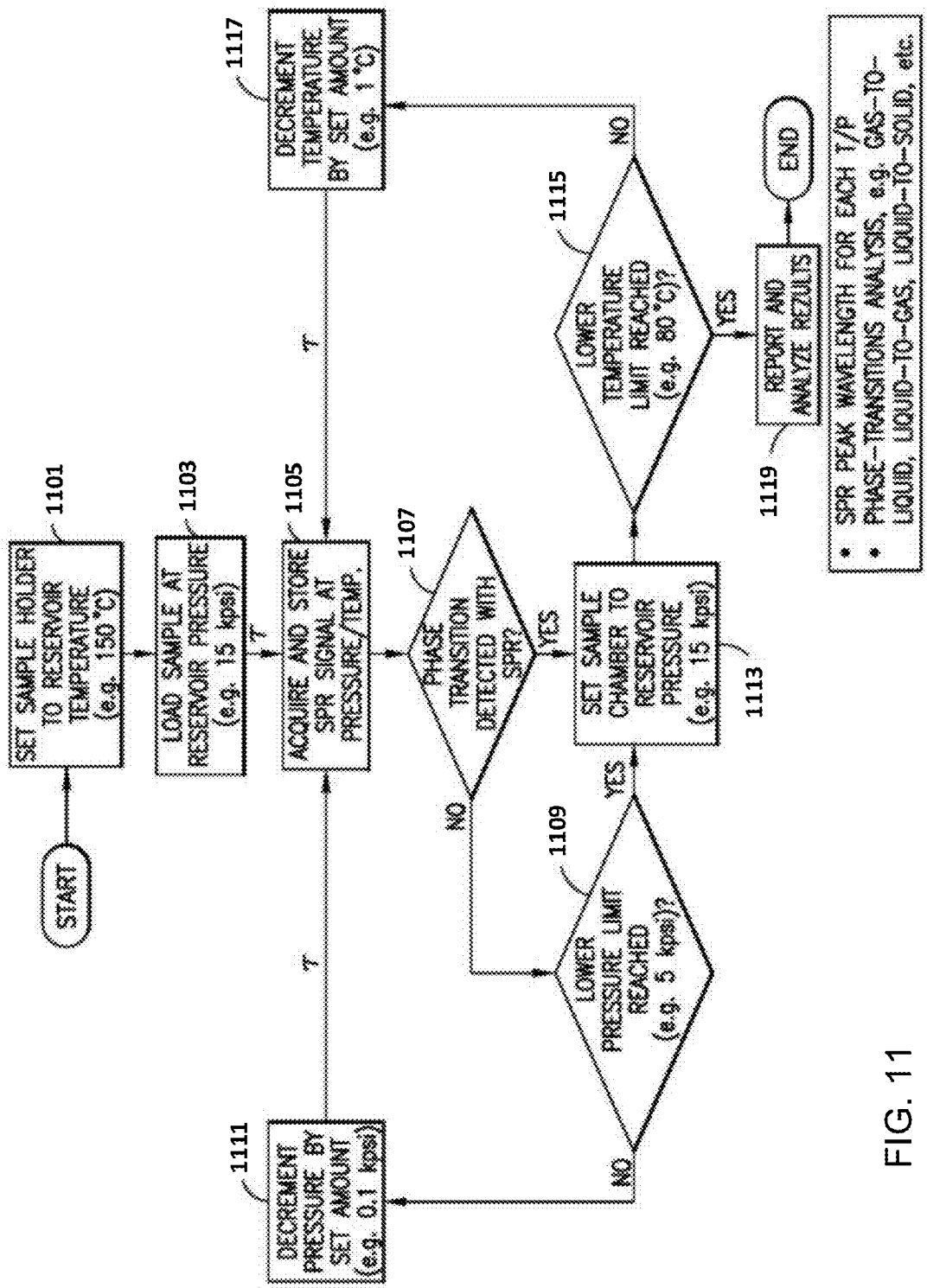
FIG. 11 is a flowchart of a workflow for detecting phase change of a reservoir fluid sample using an SPR sensor probe and associated sample handling, pressure and temperature control system.

FIG. 11 is the workflow for determining phase transitions using the SPR sensing system 700 or 800 as described herein. In block 1101, the initial temperature is set at reservoir temperature (e.g. 150° C.) and the flow line with SPR sensor probe (sample chamber) is allowed to stabilize for a thermal equilibrium time, r, before proceeding to sample loading. The thermal equilibrium time is the time required for the flow line with SPR sensor probe to reach the set temperature. Additional time may be added to the thermal equilibration time to ensure thermodynamic steady-state of the sample has been reached. In block 1103, the hydrocarbon fluid sample (~1 mL) is then charged into the flow line with SPR sensor probe at reservoir pressure (e.g., 15 kpsi) and the first SPR spectrum is acquired.

The temperature-dependent and pressure-dependent phase transitions of the hydrocarbon fluid in the flow line with SPR sensor probe can then be characterized. The flow line with SPR sensor probe is initially heated to a desired high temperature limit above the phase transition temperature—typically the sample's reservoir temperature. A pressure decrementing loop is then executed in blocks 1105 to 1111. In this loop, consecutive SPR spectra are acquired as the pressure of the flow line with SPR sensor probe is gradually and incrementally lowered, until the low pressure limit has been reached (below the phase transition). At each pressure setpoint, the assembly is allowed to reach steady state prior to acquiring the SPR spectra (block 1105), set by the equilibrium time and monitored through the pressure and temperature sensors using PID control loops with live feedback (thermocouples and pressure transducers). This is required to ensure that the temperature and pressure of the sample cell (and hydrocarbon fluid sample) corresponds to the temperature and the pressure set by the user. After a pressure loop is fully executed or a phase transition has been detected, the pressure of the sample chamber is returned to reservoir pressure in block 1113. In block 1115 and 1117, the temperature of the sample chamber is decremented by a set amount, and the pressure loop is executed again. The temperature parent loop of blocks 1115 and 1117 (along with the children pressure loops) is executed until a user specified lower temperature limit is reached. The pressure loop and temperature loop can be executed independently or in a nested manner as required by the type of phase transition targeted.

Figure 12:
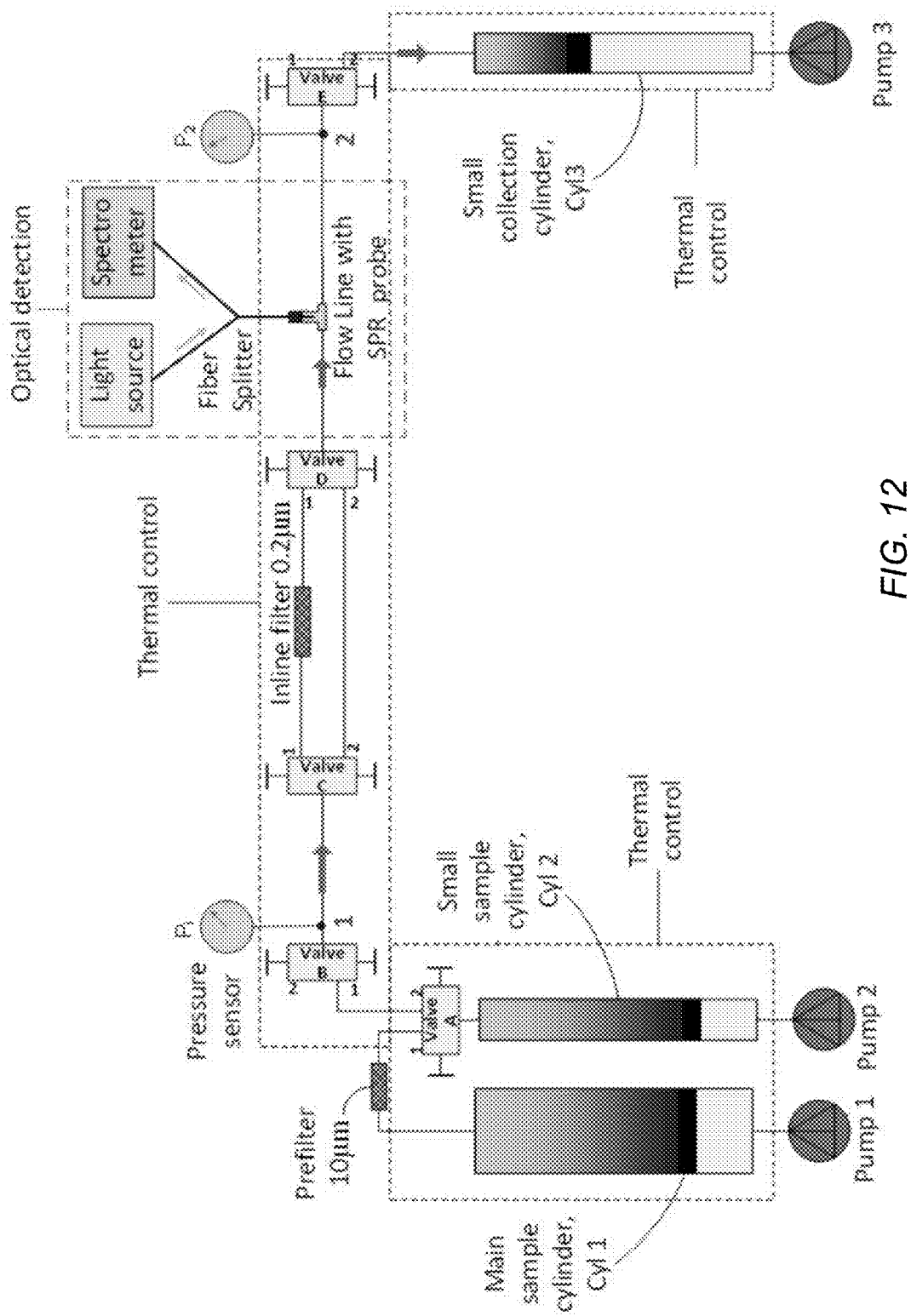
FIG. 12 is a schematic diagram of a laboratory apparatus with an SPR sensor probe.
Figure 13:
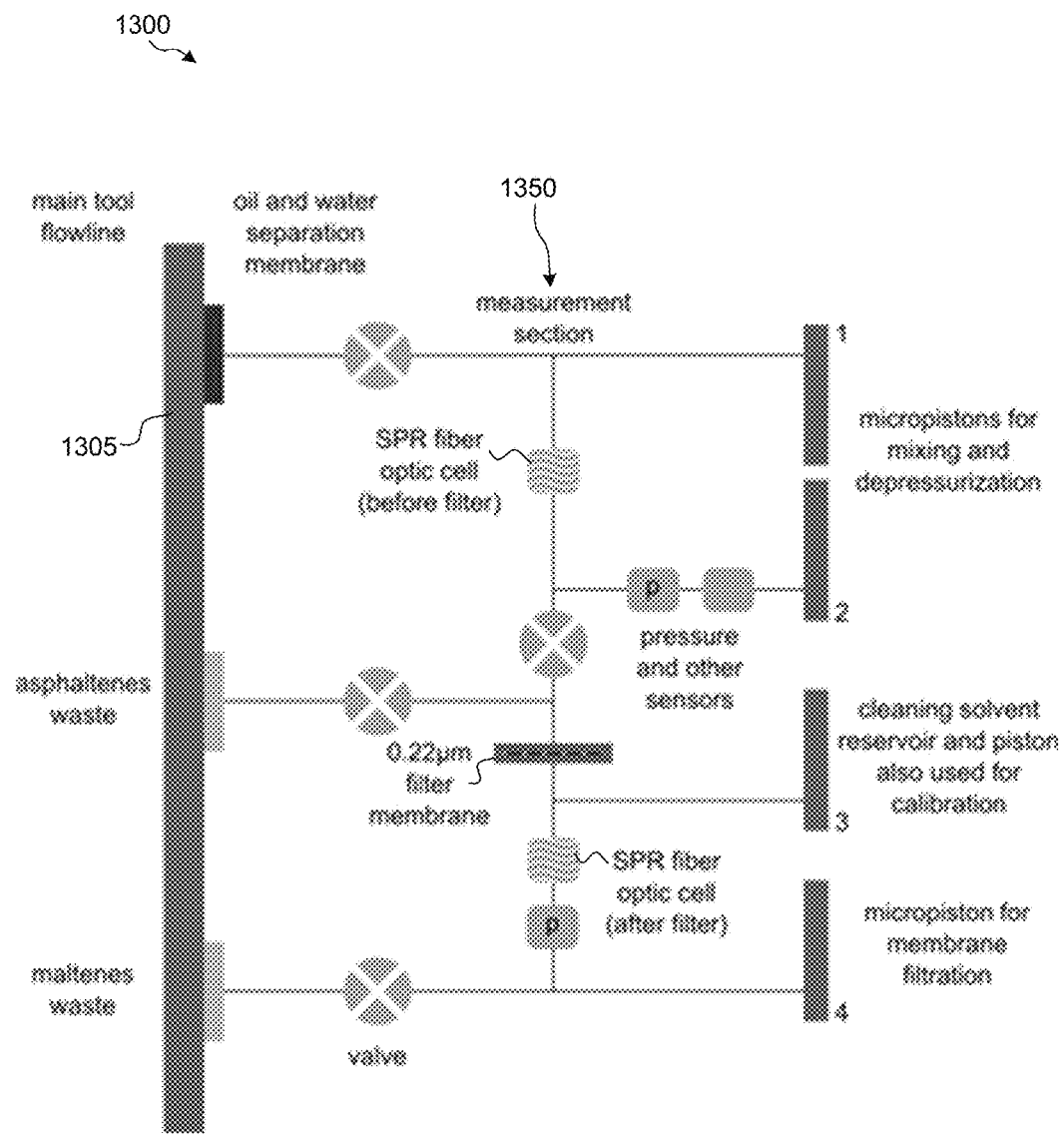
FIG. 13 is a schematic diagram of a downhole tool system with two SPR sensor probes.

The workflow of FIG. 11 can be implemented both in the laboratory and downhole. FIG. 12 shows a laboratory system and FIG. 13 shows a downhole tool implementation. The laboratory system of FIG. 12 has three sample cylinders (labelled Cyl1, Cyl2, and Cyl3) to perform sample handling. The cylinders were equipped with a floating sealed-piston. The pressure in the cylinders can be controlled using precision pumps (labelled pump1, pump2 and pump3, ISCO 65D, Teledyne ISCO, Nebraska, USA). High pressure stainless steel tubing and valves (High Pressure Equipment, Pennsylvania, USA) can be used to control the flow of sample between the cylinders. Two high pressure filters (10 μm prefilter, High Pressure Equipment, Pennsylvania, USA and VHP 0.2 μm inline filter, IDEX Health & Science, WA, USA) can be used in the setup. The flow line with SPR sensor probe of the system 700 or 800 as described herein (labeled "optical detection) is fluidly coupled between the inline filter and Cyl3 to interrogate the sample at test conditions. The SPR sensor probe can be excited with a halogen light source (HL-2000, Ocean Optics, Florida, USA) and ultraviolet-visible-near infrared spectrometer (HR2000+CG-UV-NIR, Ocean Optics, Florida, USA) to acquire the spectrum of the oil. Two gauge pressure sensors (Sensotreme GmbH, Ramsen, Switzerland, accuracy ±10 psi) can be installed in the flow lines before and after the 0.2 μm inline filter to measure the pressures at the two locations (P1 at 1 and P2 at 2). All the fluid handling components in the flow path can be maintained at isothermal conditions corresponding to reservoir temperature $T_{res}$. Such isothermal conditions can be maintained by closed loop control of a thermoelectric-based heater/cooler apparatus (or other temperature control system) that is thermally coupled to the fluid handling elements such that the fluid temperature of these fluid handling elements is maintained at the predefined isothermal conditions. The laboratory apparatus can be manually controlled or completely automated.

FIG. 13 shows a downhole tool system 1300 with two SPR sensor probes. Fluid is drawn into the downhole tool system 1300 for analysis using the main tool flowline 1305. The tool system 1300 can be provided as part of a downhole tool in a drill string, a downhole tool deployed by wireline, or some other downhole tool, such as those described above. The system 1300 can be operated according to the techniques described above to determine asphaltene onset conditions and other phase transitions for formation fluids received in the tool (e.g., by systematically depressurizing crude oil drawn into the downhole tool, filtering aggregated asphaltenes, and comparing measured optical SPR spectra). In the presently depicted embodiment, crude oil is drawn into the measurement apparatus from the main flowline 1305 through a membrane. The fluid in the flowline may include water, and the membrane of at least some embodiments is an oil-water separation membrane that inhibits flow of water to other components of the measurement apparatus. A valve controls flow of crude oil into a measurement section 1350. Various sensors, along with a pressure sensor, can be provided along the measurement section 1350 for characterizing the fluid. These sensors should be placed downstream of the first SPR sensor probe to avoid excess hold up volumes. The apparatus also includes pistons 1 and 2, which can be used for mixing and depressurization of the crude oil within the top measurement section. Pressure of the crude oil within the measurement section be changed by moving the piston 1 or 2 to change the volume of the crude oil. In some embodiments, the apparatus is a microfluidic system, in which the sensors are microfluidic sensors, the optical detection units (e.g., SPR sensor probes, spectrometers) are miniaturized units, and the pistons 1 and 2 are micropistons. The top portion of FIG. 13 (above the filter) implements the simplest SPR phase change sensor platform shown in FIG. 9.

The measurement section 1350 can also implement the SPR phase change sensor platform shown in FIG. 10. To accomplish the filtration configuration, a valve above the filter can be opened to allow the crude oil to flow through an asphaltene filter membrane. The transmembrane pressure is regulated by pistons 1, 2 and 4 to achieve suitable flow across the membrane. The filter collects aggregated asphaltenes in the crude oil, such as those formed from mixing and depressurization of the oil to a level below its AOP. Any suitable filter could be used, and the filter may be identical to the filter described above with respect to filtration unit. The pressure of the crude oil in the measurement section, before and after filtration, can be measured with two pressure sensors. The SPR spectra of the crude oil can be determined by the two SPR sensor probes upstream and downstream from the filter, but the tool can also be operated with only the downstream SPR sensor probe. An additional solvent filled reservoir and piston 3 can be used to backflush the membrane and clean the tool via various valve configurations. The same cleaning solvent can also be used as a calibration reference for the SPR sensor probes, having a known refractive index and the corresponding SPR peak wavelength. Two waste ports are used to return fluids back to the main tool flowline, prefilter—called asphaltenes waste, and postfilter—called maltenes waste.

Figure 14A:
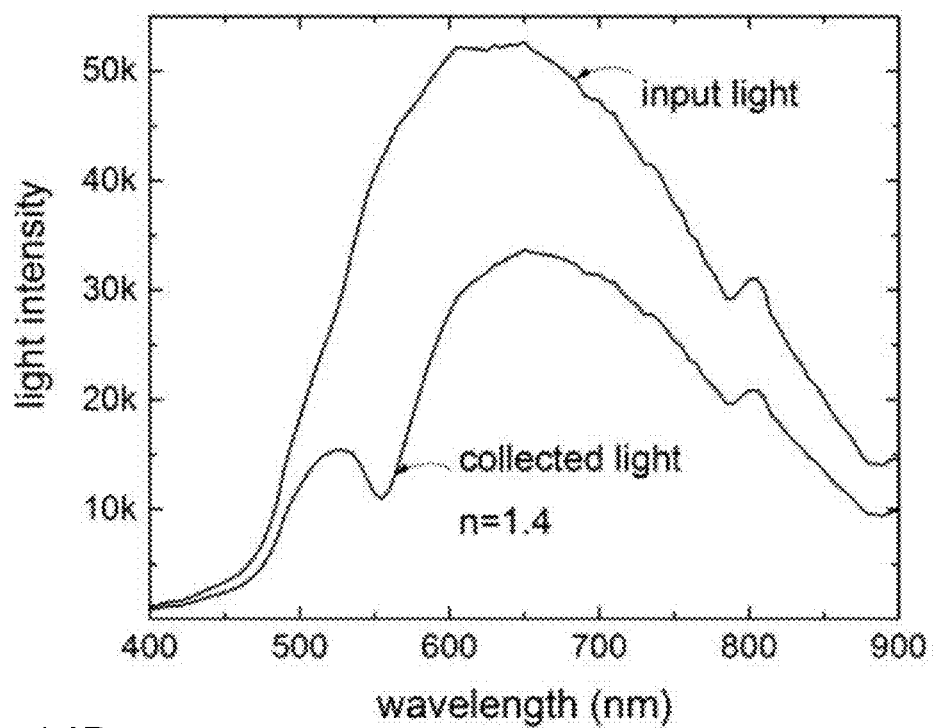
FIGS. 14A, 14C and 14E are graphs that show the reflected or transmitted spectra (labeled "collected light) and the reference spectra (labeled "input light") as measured by the spectrometers of the SPR sensing systems of FIG. 7A or 8A for a reservoir fluid sample that is experiencing phase change.
Figure 14B:
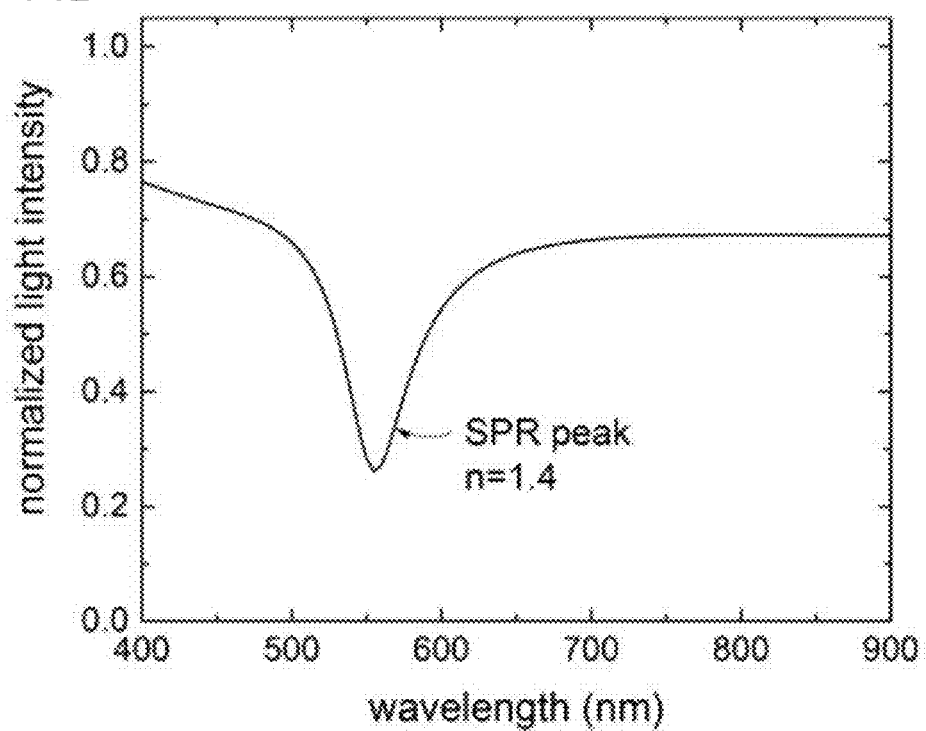
FIGS. 14B, 14D and 14F show the corresponding change in SPR peak wavelength determined by the SPR sensing systems of FIG. 7A or 8A based on analysis of the reflected or transmitted spectra and the reference spectra for the reservoir fluid sample that is experiencing phase change.
Figure 14C:
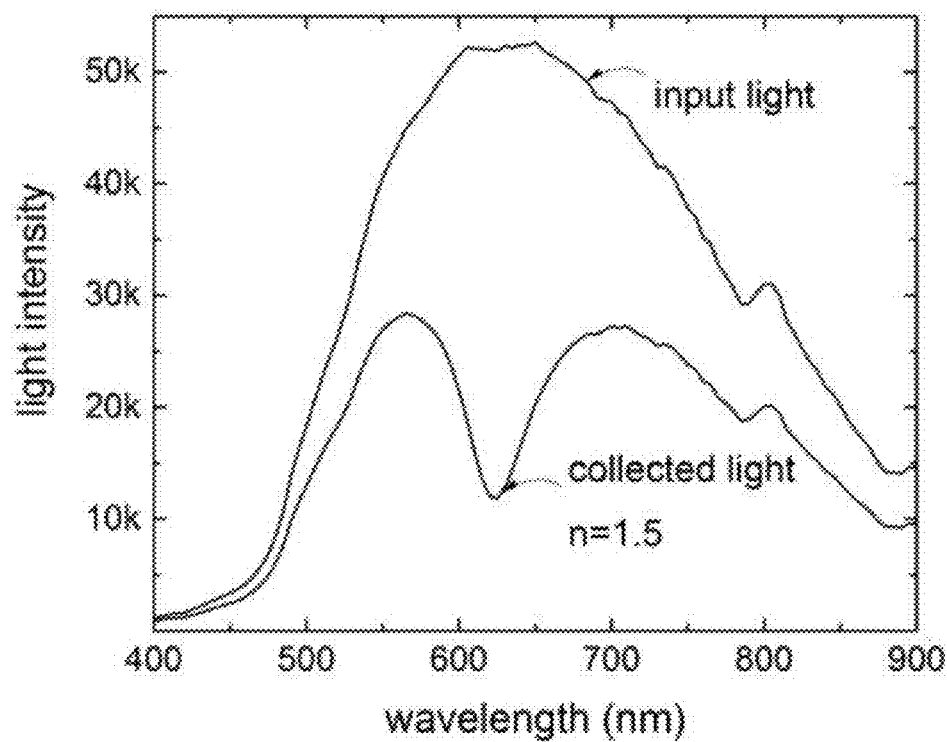
Figure 14D:
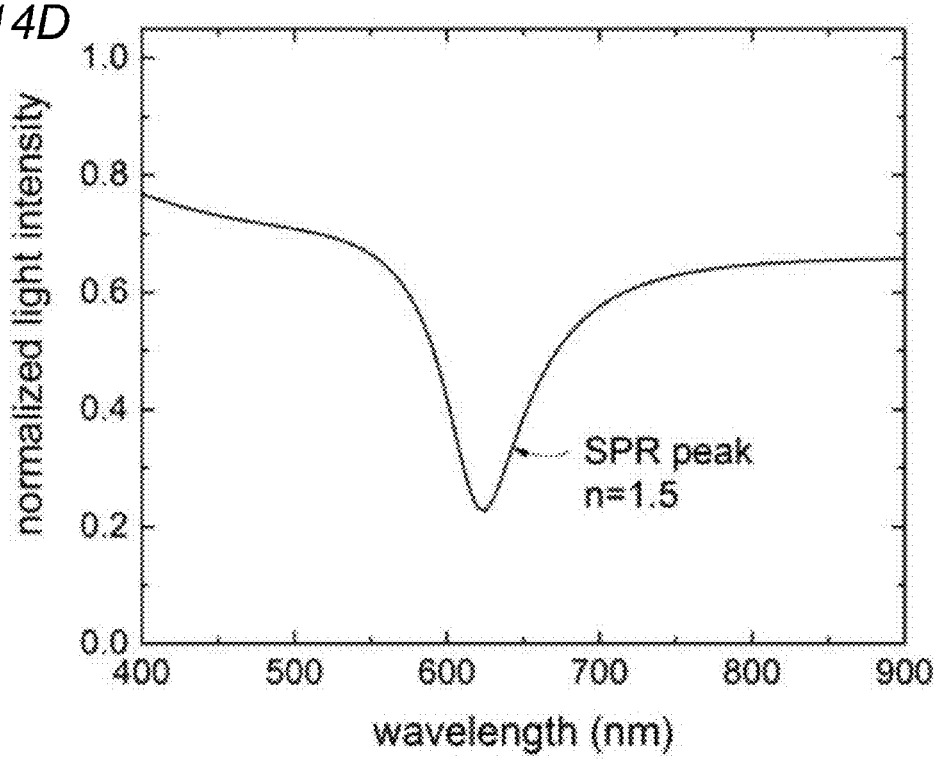
Figure 14E:
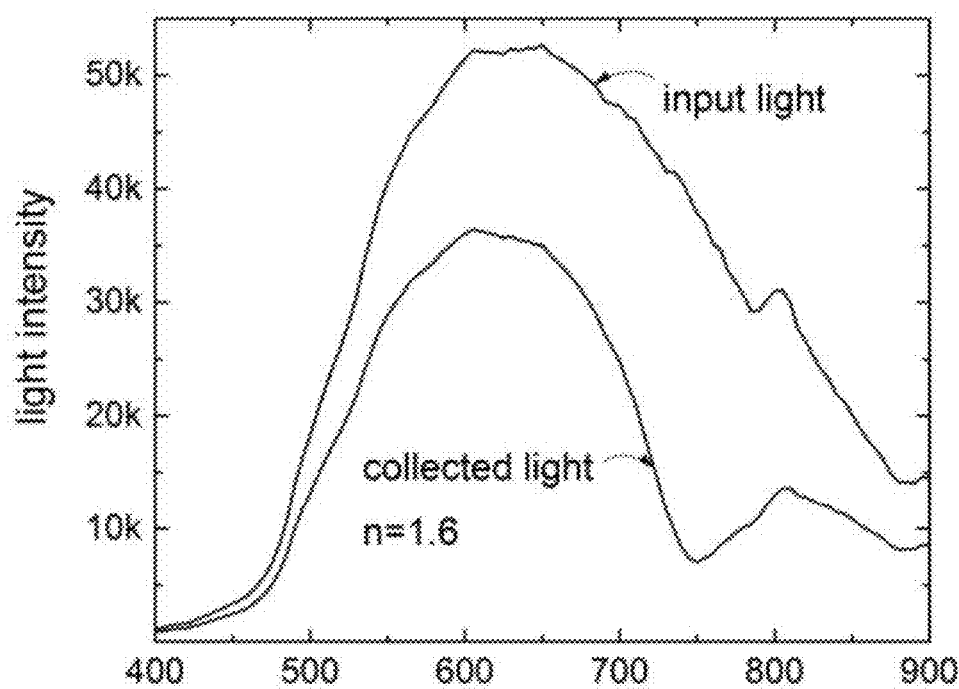
Figure 14F:
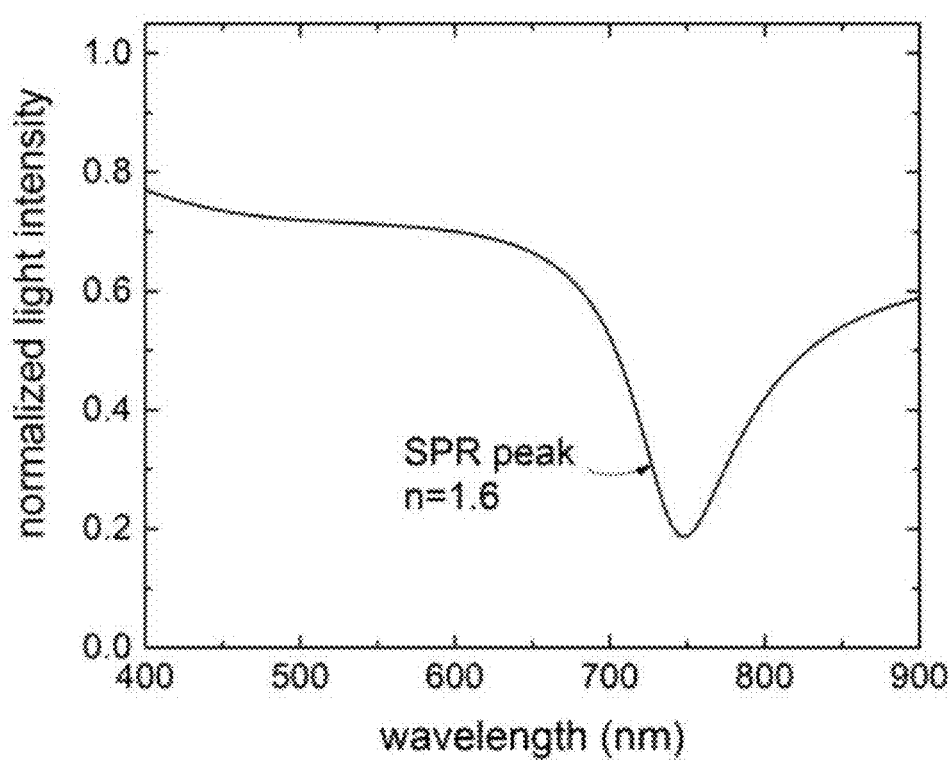

FIGS. 14A, 14C and 14E show the reflected or transmitted spectra (labeled "collected light") and the reference spectra (labeled "input light") as measured by the spectrometers of the SPR sensing system 700 or 800 for a reservoir fluid sample that is experiencing phase change. FIGS. 14B, 14D and 14F show the corresponding change in SPR peak wavelength determined by the SPR sensing system 700 or 800 based on analysis of the reflected or transmitted spectra and the reference spectra for the reservoir fluid sample that is experiencing phase change.

Oilfield Systems

Figure 16:
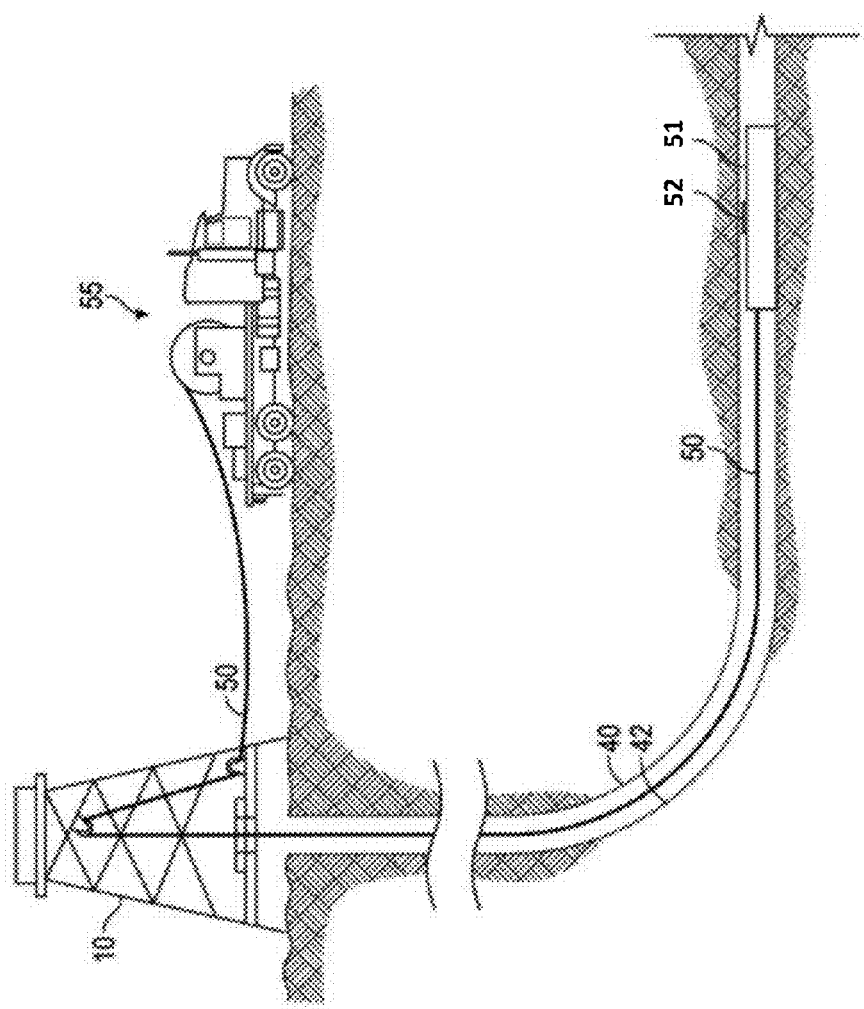
FIG. 16 is a schematic diagram showing one example of a rig on which disclosed downhole tool embodiments may be utilized.

FIG. 16 depicts a rig 10 suitable for employing certain downhole tool embodiments disclosed herein. In the depiction, rig 10 is positioned over (or in the vicinity of) a subterranean oil or gas formation (not shown). The rig may include, for example, a derrick and a hoisting apparatus for lowering and raising various components into and out of the wellbore 40. A downhole tool 51 is deployed in the wellbore 40. The downhole tool 51 may be connected to the surface, for example, via coiled tubing 50 which is in turn coupled to a coiled tubing truck 55.

During operation, the downhole tool 51 may be lowered into the wellbore 40. In a highly deviated borehole, the downhole tool 51 may alternatively or additionally be driven or drawn into the borehole, for example, using a downhole tractor or other conveyance means. The disclosed embodiments are not limited in this regard. For example, the downhole tool 51 may also be conveyed into the borehole 40 using drill pipe, a wireline cable or other conveyance methodologies.

The example downhole tool 51 described herein may be used to obtain and analyze samples of formation fluids in situ. For example, the formation fluid samples can include natural gas, various gas mixtures, oil or various oil mixtures. The downhole tool 51 can include a probe assembly 52 for establishing fluid communication between the downhole tool 51 and the subsurface formation. During operation, the probe assembly 52 may be extended into contact with the borehole wall 42 (e.g., through a mud cake layer). Formation fluid samples may enter the downhole tool 51 through the probe assembly 52 (e.g., via a pumping or via formation pressure). The downhole tool 51 also includes an SPR sensor 1740 (FIG. 17) for measuring at least one property relating to phase change of formation fluid sample that enters the downhole tool 51 through the probe assembly 52.

The probe assembly 52 may include a probe mounted in a frame (the individual probe assembly components are not shown). The frame may be configured to extend and retract radially outward and inward with respect to the sampling tool body. Moreover, the probe may be configured to extend and retract radially outward and inward with respect to the frame. Such extension and retraction may be initiated via an uphole or downhole controller. Extension of the frame into contact with the borehole wall 42 may further support the sampling tool in the borehole as well as position the probe adjacent the borehole wall 42.

In some embodiments, such as those used in low permeability formations, the probe assembly 52 may be replaced by packer assembly (not shown). The disclosed embodiments are not limited in this regard. As is known to those of ordinary skill in the art, a packer assembly, when inflated, is intended to seal and/or isolate a section of the borehole wall to provide a flow area with which to induce fluid flow from the surrounding formation.

The downhole tool 51 can also include a downhole telemetry subsystem (not shown) that communicates data signals and control signals between the downhole tool 51 and a surface-located data acquisition and control system, which can be part of the truck 55 or other surface-located system. The downhole telemetry subsystem can employ a variety of telemetry methods, such as wired telemetry methods that employ telemetry cables, drill pipe that incorporate telemetry cables, or fiber optic cables, and wireless telemetry methods, such as mud-pulse telemetry methods, electromagnetic telemetry methods, and acoustic telemetry methods. The downhole telemetry subsystem can also supply electrical power supply signals generated by a surface-located power source for supply to the downhole tool 51. The surface-located power source can be part of the truck 55 or other surface-located system. The downhole tool 51 can also include a power supply transformer/regulator for transforming the electric power supply signals supplied by the surface-located power source to appropriate levels suitable for use by the electrical components of the downhole tool 100. In alternate embodiments, the downhole tool 51 can include a downhole power source supply (such as a battery or turbine generator and/or energy harvester for logging while drilling tools) that supplies electrical power supply signals to the downhole tool 51.

While FIG. 16 depicts a particular downhole tool 51, it will be understood that the disclosed embodiments are not so limited. For example, downhole tool 51 may include a drilling tool such as a measurement while drilling or logging while drilling tool configured for deployment on a drill string. The disclosed embodiments are not limited in these regards.

Figure 17:
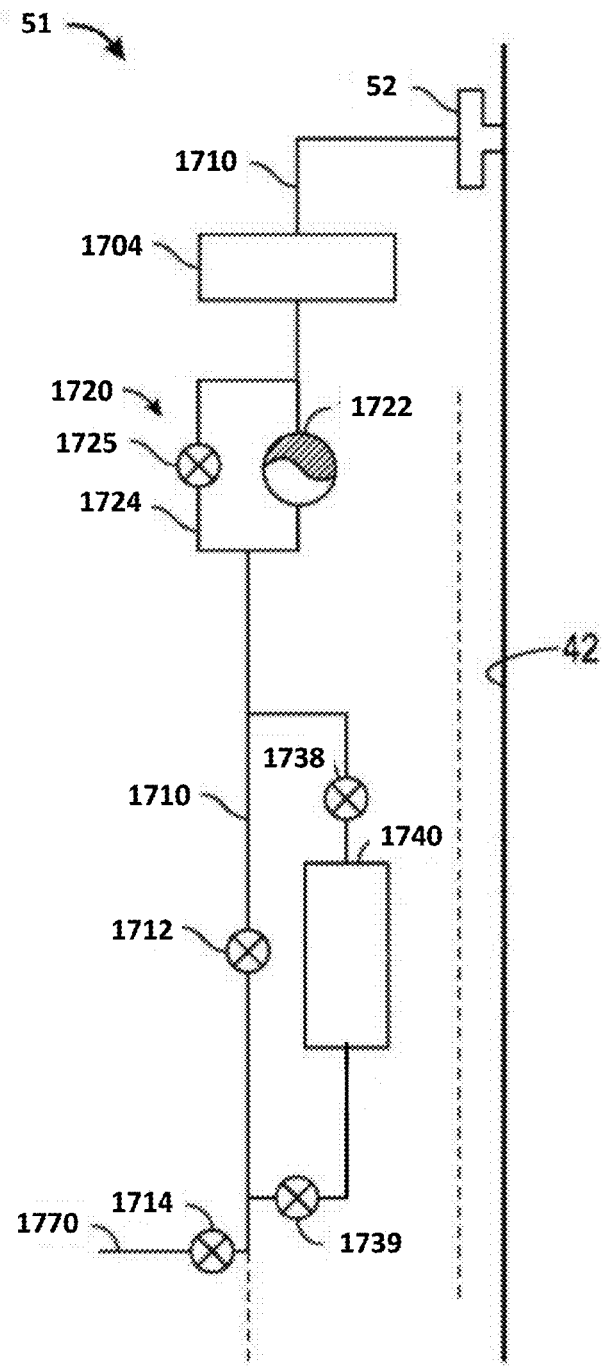
FIG. 17 is a schematic fluid flow circuit diagram of the downhole tool of FIG. 16 in which disclosed SPR sensor embodiments may be utilized.

FIG. 17 shows the fluid flow circuit of the downhole tool 51 of FIG. 16. The probe assembly 52 is depicted as being in contact with borehole wall 42 for obtaining a formation fluid sample. In the depicted embodiment, probe assembly 52 is in fluid communication with a primary flow line 1710 including a fluid analysis module 1704 and a fluid pumping module 1720. The fluid pumping module 1720 is in fluid communication with the probe 52 and includes a pump 1722 and a bypass flow line 1724 with bypass valve 1725 that are coupled in parallel with one another as depicted. The SPR sensor 1740 is in fluid communication with primary flow line 1710 and may be configured to receive a formation fluid sample. The downhole tool 51 can further include an isolation valve 1712 that is part of the primary flow line 1710 as well as a discharge valve 1714 and a fluid outlet line 1770 that are fluidly coupled to the primary flow line 1710 as shown. The discharge valve 1714 and the fluid outlet line 1770 can be configured for discharging unwanted formation fluid into the annulus or into the subterranean formation. The downhole tool 51 may further include one or more sample bottles (not shown on FIG. 17) that are fluidly coupled to the primary flow line 1710 by associated valves and have various functionality, such as, for example, zero dead volume (flashing line), self-sealing functionality, and/or being nitrogen-charged as is well known.

The probe assembly 52 may be engaged with the borehole wall 42 as depicted so as to establish fluid communication between the subterranean formation and the primary flow line 1710 (those of ordinary skill will readily appreciate that the probe assembly may penetrate a mud cake layer on the borehole wall so as to obtain fluid directly from the formation). Examples of probes suitable for use in the in the disclosed embodiments include the Single-Probe Module or Dual-Probe Module included in the Schlumberger MDT® or described in U.S. Pat. Nos. 4,860,581 and 6,058,773, which are fully incorporated by reference herein. While not depicted it will be understood that the probe assembly may include or more probes coupled to a frame that may be extended and retracted relative to a tool body. In the depicted embodiment, probe assembly 52 is an inlet probe that provides a flow channel from the subterranean formation to the primary flow line 1710. The downhole tool 51 may further include one or more outlet probes (e.g., at the downstream end of the fluid outlet line 1770) so as to provide a channel through which fluid may flow from the primary flow line 1710 out of the tool 51 and back into the formation. In such an embodiment, fluid may be circulated from the formation into the primary flow line 1710 and back into the formation.

Fluid analysis module 1704 may include substantially any suitable fluid analysis sensors and/or instrumentation, for example, including chemical sensors, optical fluid analyzers, optical spectrometers, nuclear magnetic resonance devices, a conductivity sensor, a temperature sensor, a pressure sensor. More generally, fluid analysis module 1704 may include substantially any suitable device that yields information relating to the composition of the formation fluid such as the thermodynamic properties of the fluid, conductivity, density, viscosity, surface tension, pressure, temperature, and phase composition (e.g., liquid versus gas composition or the gas content) of the fluid. While not depicted, it will be understood that fluid analysis sensors may alternatively and/or additionally be deployed on the downstream side of the fluid pumping module, for example, to sense fluid property changes that may be induced via pumping.

Fluid pumping module 1720 may include substantially any suitable pump 1722. For example, the pump 1722 may include a reciprocating piston pump, a retractable piston pump, or a hydraulic powered pump.

The SPR sensor 1740 is fluidly coupled to the primary flow line 1710 by an intake valve 1738 and an exhaust valve 1739. The SPR sensor 1740 can be embodied by any one of the SPR sensors described herein (e.g., the SPR sensor of FIG. 1 or the SPR probe sensors of FIGS. 7A and 8A) and configured to measure at least one property relating to phase change of formation fluid sample obtained via the probe 52 and the primary flow line 1610.

Figure 18:
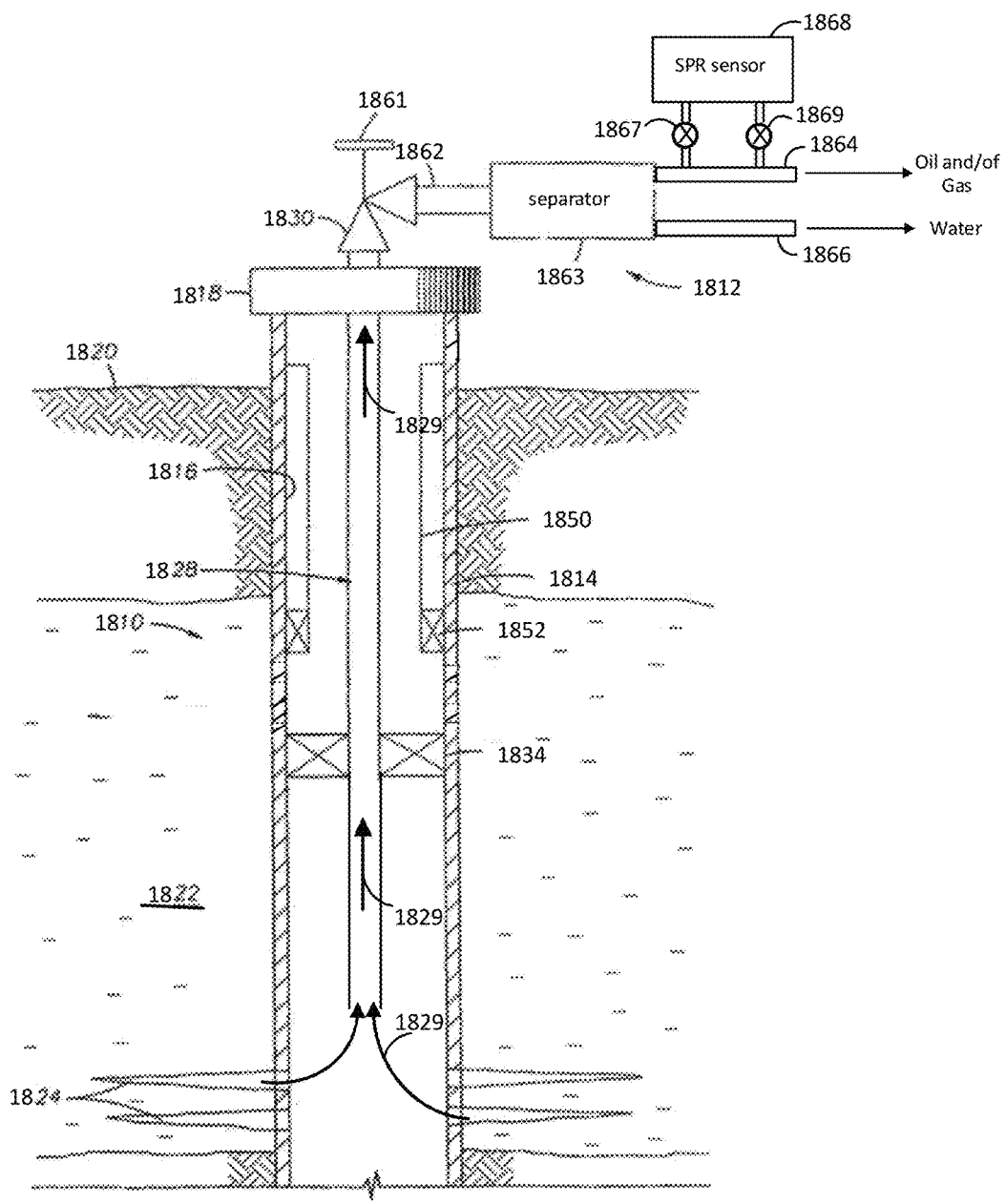
FIG. 18 is a schematic diagram showing one example of a production well in which disclosed SPR sensor embodiments may be utilized.

Referring to FIG. 18, an exemplary hydrocarbon production well 1810 is shown, which includes a wellbore casing 1814, which typically includes a number of concentric casing strings (not shown). The casing 1814 defines an annulus 1816 that extends downward from a wellbore opening or entrance 1818 at the surface 1820. It is noted that the surface 1820 may be either the surface of the earth, or, in the case of a subsea well, the seabed. The casing 1814 extends through a hydrocarbon production zone 1822 from which it is desired to acquire production fluid. The casing 1814 has perforations 1824 disposed therethrough so that production fluid may enter the annulus 1816 from the production zone 1822.

Production tubing 1828 is disposed downward within the annulus 1816 supported from a wellhead 1830 at the surface 1820. A production tubing packer 1834 is set above the perforations 1824 to establish a fluid seal between the production tubing 1828 and the casing 1814. The production tubing 1828 includes at least one fluid inlet below the packer 1834 which permits fluid communication from the annulus 1816 into the interior of the production tubing 1828 to allow production fluid to flow to the wellhead 1830 (indicates as arrows 1829) due to the formation pressure. In other embodiments, artificial lift (such sucker-rod (beam) pumping, electrical submersible pumping (ESP), gas lift and intermittent gas lift, reciprocating and jet hydraulic pumping systems, plunger lift, and progressive cavity pumps (PCP)), can be used to generate or assist in flowing the production fluid through the interior of the production tubing 1828 to the wellhead 1830.

The upper portion of the production tubing 1828 may optionally be surrounded by liner or sleeve 1850 which extends from the well opening 1818 downward within the annulus 1816. A packer 1852 can be set at the lower end of the sleeve 1850 to establish a fluid seal between the sleeve 1850 and the casing 1814. The sleeve 1850 can provide additional isolation between the annulus 1816 and any fresh water aquifers.

The wellhead 1830 can include an adjustable choke 1861 of a type known in the art which is used to control the flow of production fluids through the wellhead 1830. A lateral fluid flowline 1862 extends from the wellhead 1830 to the separator assembly 1863.

The separator assembly 1863 separates the gas/oil and water components of the production fluids supplied thereto, which are output by corresponding flowlines 1864, 1866 as shown. The flowlines 1864 and 1866 carry the respective gas/oil and water components of the production fluids to other surface-located facilities (not shown). Such surface-located facilities can include fluid collection systems (such as tanks), fluid processing devices and/or pipelines.

An SPR sensor 1868 is fluidly coupled to the flow line 1864 by an intake valve 1867 and an exhaust valve 1869. The SPR sensor 1864 can be configured to receive a sample of the gas/oil components of the production fluids that is output by the separator 1863 and carried by the flowline 1864. The SPR sensor 1840 can be embodied by any one of the SPR sensors described herein (e.g., the SPR sensor of FIG. 1 or the SPR probe sensors of FIGS. 7A and 8A) and configured to measure at least one property relating to phase change of production fluid sample obtained via the flowline 1864.

Computer Systems

Note that parts of the SPR sensors and systems as described above can be implemented as computer program executed by a computer processing platform (e.g., the computing system 123 of FIG. 1). The computer program may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processing platform. The computer instructions may be distributed in any form as a removable storage medium with accompanying printed or electronic documentation (e.g., shrink wrapped software), preloaded with a computer system (e.g., on system ROM or fixed disk), or distributed from a server over a communication system (e.g., the Internet or World Wide Web).

The computer processing platform may include a CPU, other integrated circuitry (e.g., Application Specific Integrated Circuits (ASIC)), programmable logic devices (e.g., a Field Programmable Gate Arrays (FPGA) and/or discrete electronic components coupled to a printed circuit board. Any of the methods and processes described above can be implemented using such logic devices.

Figure 19:
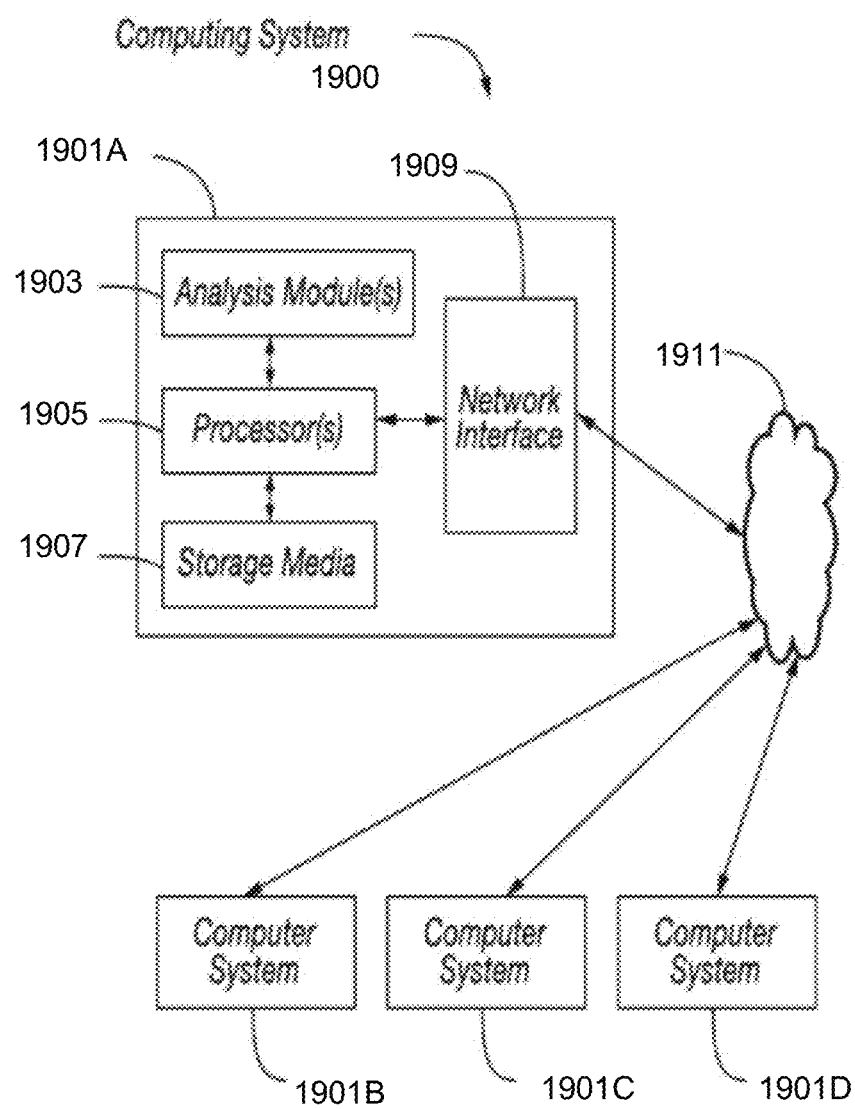
FIG. 19 is a schematic block diagram of a computer processing platform that can be used as part of the disclosed SPR sensor embodiments.

FIG. 19 shows an example computing system 1900 that can be used to implement the computer processing platforms of the SPR sensors as described herein. The computing system 1900 can be an individual computer system 1901A or an arrangement of distributed computer systems. The computer system 1901A includes one or more analysis modules 1903 (a program of computer-executable instructions and associated data) that can be configured to perform various tasks according to some embodiments, such as the tasks described herein. To perform these various tasks, an analysis module 1903 executes on one or more processors 1905, which is (or are) connected to one or more storage media 1907. The processor(s) 1905 can be connected to a network interface 1909 to allow the computer system 1901A to communicate over a data network 1911 with one or more additional computer systems and/or computing systems, such as 1901B, 1901C, and/or 1901D. Note that computer systems 1901B, 1901C and/or 1901D may or may not share the same architecture as computer system 1901A, and may be located in different physical locations.

The processor 1905 can include at least a microprocessor, microcontroller, processor module or subsystem, programmable integrated circuit, programmable gate array, digital signal processor (DSP), or another control or computing device.

The storage media 1907 can be implemented as one or more non-transitory computer-readable or machine-readable storage media. Note that while in the embodiment of FIG. 19 the storage media 1907 is depicted as within computer system 1901A, in some embodiments, the storage media 1907 may be distributed within and/or across multiple internal and/or external enclosures of computing system 1901A and/or additional computing systems. Storage media 1907 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the computer-executable instructions and associated data of the analysis module(s) 1903 can be provided on one computer-readable or machine-readable storage medium of the storage media 1907, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

The computing system 1900 can also include one or more display devices that are configured to display information produced by the various tasks according to some embodiments, such as the tasks described herein. For example, the display device can display plots or other visual representations of the intensity data or spectra produced by the various SPR sensor embodiments for human evaluation of the data as desired.

It should be appreciated that computing system 1900 is only one example of a computing system, and that computing system 1900 may have more or fewer components than shown, may combine additional components not depicted in the embodiment of FIG. 19, and/or computing system 1900 may have a different configuration or arrangement of the components depicted in FIG. 19. The various components shown in FIG. 19 may be implemented in hardware, software, or a combination of both hardware and software, including one or more signal processing and/or application specific integrated circuits.

Modifications

Although only a few examples have been described in detail above, those skilled in the art will readily appreciate that many modifications are possible in the examples without materially departing from this subject disclosure.

In another example, an SPR sensor can perform measurements utilizing monochromatic light at multiple wavelengths. In this case, each wavelength probes a different distance into the SPR sensing region, which can allow for determination of the thickness of solid precipitation Also, the methods and systems described herein are not limited to analyzing a set of particular fluids. Various embodiments of methods and systems described herein can be used to analyze hydrocarbons (e.g., dark oils, heavy oils, volatile oils, and black oils).

Furthermore, various embodiments of the present disclosure are not limited to oil and gas field applications.

Also, the fluid handling elements (such as reservoirs, tanks, pumps, valves and flow lines) of the SPR sensors as described herein can be computer controlled or manually controlled to provide for pressure control of the fluids flowing through the SPR sensor. Furthermore, the temperature control elements of the SPR sensors as described herein can be computer controlled or manually controlled to provide for temperature control of the fluids flowing through the SPR sensor.

Although several example embodiments have been described in detail above, those skilled in the art will readily appreciate that many modifications are possible in the example embodiments without materially departing from the scope of this disclosure. Moreover, the features described herein may be provided in any combination.

Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. An optical sensor comprising:
a flow cell that is configured to permit flow of a hydrocarbon-based analyte through the flow cell;
a metallic film disposed adjacent or within the flow cell;
a light source configured to generate polychromatic light;
at least one optical element configured to direct polychromatic light produced by the light source for supply to an interface of the metallic film under conditions of surface plasmon resonance and to direct polychromatic light reflected at the interface of the metallic film for output from the at least one optical element, wherein the polychromatic light reflected at the interface of the metallic film is sensitive to surface plasmon resonance at the interface of the metallic film in order to provide an surface plasmon resonance (SPR) sensing region within the flow cell;
at least one spectrometer operably coupled to the at least one optical element, wherein the at least one spectrometer is configured to measure spectral data of polychromatic light reflected at the interface of the metallic film as output by the least one optical element; and a computer processing system operably coupled to the at least one spectrometer, wherein the computer processing system is configured to process the spectral data measured by the at least one spectrometer over time as the hydrocarbon-based analyte flows through the flow cell to determine SPR peak wavelength over time, and wherein the computer processing system processes the SPR peak wavelength over time to determine at least one property related to phase transition of the hydrocarbon-based analyte.

2. An optical sensor according to claim 1, wherein:
the at least one optical element comprises a prism disposed adjacent the metallic film.

3. An optical sensor according to claim 2, wherein:
the prism comprises a dove prism.

4. An optical sensor according to claim 2, wherein:
the metallic film is part of a multilayer structure formed on one side of a substrate, wherein the multilayer structure interfaces to the flow cell and the opposite side of the substrate is disposed adjacent the prism.

5. An optical sensor according to claim 4, further comprising:
an index matching fluid disposed between the opposite side of the substrate and the prism.

6. An optical sensor according to claim 1, wherein:
the least one optical element comprises a fiber optic core, wherein the metallic film is bonded to the fiber optic core.

7. An optical sensor according to claim 6, wherein:
the metallic film is part of a multilayer structure bonded to the fiber optic core.

8. An optical sensor according to claim 7, wherein:
the multilayer structure surrounds a lengthwise segment of the fiber optic core; and
the lengthwise segment of the fiber optic core directs polychromatic light to the metallic film of the surrounding multilayer structure for reflection at the interface of the metallic film of the surrounding multilayer structure.

9. An optical sensor according to claim 8, wherein:
the least one optical element further comprises a mirror formed at one end of the fiber optic core, wherein the mirror is configured to return polychromatic light reflected at the interface of the metallic film of the surrounding multilayer structure for output to a spectrometer.

10. An optical sensor according to claim 9, wherein:
the mirror is formed from the same metal as the metallic film of the multilayer structure.

11. An optical sensor according to claim 8, wherein:
the fiber optic core is configured to transmit polychromatic light reflected at the interface of the metallic film of the surrounding multilayer structure for output to a spectrometer.

12. An optical sensor according to claim 6, wherein:
the fiber optic core and metallic film are part of a probe assembly that extends into the flow cell.

13. An optical sensor according to claim 12, wherein:
the probe assembly extends into the flow cell in a direction parallel to the flow through the flow cell.

14. An optical sensor according to claim 12, wherein:
the probe assembly extends into the flow cell in a direction transverse to the flow through the flow cell.

15. An optical sensor according to claim 12, further comprising:
a seal that provides a fluid seal between the probe assembly and the flow cell.

16. An optical sensor according to claim 1, wherein:
the metallic film is part of a multilayer structure that interfaces to the flow cell or that extends into the flow cell.

17. An optical sensor according to claim 1, wherein:
the multilayer structure includes a thin-film stack including a protective layer that covers the metallic film and/or a bonding layer formed under the metallic film.

18. An optical sensor according to claim 17, wherein:
the protective layer is present and comprises Zirconium Dioxide.

19. An optical sensor according to claim 17, wherein:
the bonding layer is present and comprises Titanium.

20. An optical sensor according to claim 1, wherein:
the metallic film comprises gold or silver.

21. An optical sensor according to claim 1, further comprising:
a polarizer coupled to the at least one optical element, wherein the polarizer is configured to split polychromatic light reflected at the interface of the metallic film into an s-polarized beam and a p-polarized beam.

22. An optical sensor according to claim 21, wherein:
the at least one spectrometer comprise a first spectrometer and a second spectrometer, the first spectrometer configured to measure spectral data of the s-polarized beam, and the second spectrometer configured to measure spectral data of the p-polarized beam; and
the computer processing system is operably coupled to the first and second spectrometers and is configured to determine an absorbance spectrum for a given time interval by subtracting spectral data of the s-polarized beam from spectral data of the p-polarized beam.

23. An optical sensor according to claim 22, wherein:
the computer processing system is configured to identify a peak in the absorbance spectrum over time in order to determine the SPR peak wavelength over time.

24. An optical sensor according to claim 1, further comprising:
a fiber splitter that directs polychromatic light produced by the light source for supply to the interface of the metallic film.

25. An optical sensor according to claim 24, wherein:
the fiber splitter directs polychromatic light produced by the light source to a first spectrometer; and
the fiber splitter directs polychromatic light reflected at the interface of the metallic film for output to a second spectrometer.

26. An optical sensor according to claim 25, wherein:
the computer processing system is configured to determine an absorbance spectrum for a given time interval by subtracting spectral data determined by measurements of the first spectrometer from spectral data determined by measurements of the second spectrometer.

27. An optical sensor according to claim 26, wherein:
the computer processing system is configured to identify a peak in the absorbance spectrum over time in order to determine the SPR peak wavelength over time.

28. An optical sensor according to claim 1, wherein:
the hydrocarbon-based analyte is mixture of an asphaltene precipitant and crude oil with varying volume fractions of asphaltene precipitant over time; and
the at least one property related to phase transition of the hydrocarbon-based analyte characterizes asphaltene deposition onset of the crude oil.

29. An optical sensor according to claim 1, wherein:
the computer processing system is further configured to employ a model that relates SPR peak wavelength to a refractive index of the crude oil.

30. An optical sensor according to claim 29, wherein:
the model is calibrated by experiments with mixtures of an asphaltene precipitant and asphaltene solvent at different relative volume fractions such that SPR peak wavelengths produced by the model matches measured SPR peak wavelengths determined by the computer processing system.

31. An optical sensor according to claim 29, wherein:
the computer processing system is further configured to employ a correlation function that relates the refractive index of the crude oil to a density of the crude oil.

32. An optical sensor according to claim 1, wherein the at least one property related to phase transition of the hydrocarbon-based analyte is associated with at least one of:
  i) detection of the formation of vapor or liquid phases of the hydrocarbon-based analyte induced by temperature and/or pressure changes;
  ii) detection of liquid condensation from hydrocarbon vapors induced by temperature and/or pressure changes;
  iii) detection of hydrate formation induced by temperature and/or pressure changes;
  iv) detection of scaling or inorganic precipitation induced by composition, temperature and/or pressure changes;
  v) detection of asphaltene onset induced by composition, temperature and/or pressure or changes; and
  vi) sample fluid typing by means of measuring the direction and/or magnitude of the SPR shift when undergoing phase change.

33. An optical sensor according to claim 1, further comprising:
a pressure control system for controlling pressure of the hydrocarbon-based analyte flowing through the flow cell over time.

34. An optical sensor according to claim 33, wherein:
the pressure control system is configured to vary pressure conditions of the hydrocarbon-based analyte flowing through the flow cell over one or more time intervals.

35. An optical sensor according to claim 33, wherein:
the pressure control system is configured to maintain constant pressure conditions of the hydrocarbon-based analyte flowing through the flow cell over one or more time intervals.

36. An optical sensor according to claim 1, further comprising:
a temperature control system for controlling temperature of the hydrocarbon-based analyte flowing through the flow cell over time.

37. An optical sensor according to claim 36, wherein:
the temperature control system is configured to vary temperature conditions of the hydrocarbon-based analyte flowing through the flow cell over one or more time intervals.

38. An optical sensor according to claim 36, wherein:
the temperature control system is configured to maintain constant temperature pressure conditions of the hydrocarbon-based analyte flowing through the flow cell over one or more time intervals.

* * * * *